United States Patent [19]

Blithe et al.

[11] Patent Number: 5,674,983
[45] Date of Patent: Oct. 7, 1997

[54] NATURAL HUMAN CHORIONIC GONADOTROPIN β-CORE MOLECULE

[75] Inventors: Diana L. Blithe, Silver Spring, Md.; Robert E. Wehmann, Brooklyn, N.Y.; Bruce C. Nisula, Rockville, Md.

[73] Assignee: The United States of America as represented by the Department of Health and Human Services, Washington, D.C.

[21] Appl. No.: 448,079

[22] Filed: May 23, 1995

Related U.S. Application Data

[60] Division of Ser. No. 789,835, Nov. 12, 1992, Pat. No. 5,445,968, which is a continuation-in-part of Ser. No. 292,985, Jan. 3, 1989, abandoned.

[51] Int. Cl.$^6$ .................. C07K 16/00; G01N 33/53
[52] U.S. Cl. .................. 530/398; 530/397; 530/399; 530/324; 530/350; 530/388.24; 530/389.2; 436/510; 436/549; 436/548; 436/814; 135/7.1; 135/975
[58] Field of Search ............... 530/398, 397, 530/399, 313, 324, 350, 388.24, 389.2; 436/510, 547, 548, 814; 435/7.1, 975

[56] References Cited

U.S. PATENT DOCUMENTS

| | | | |
|---|---|---|---|
| 4,565,687 | 1/1986 | Khazaeli | 424/1.1 |
| 4,804,626 | 2/1989 | Bellet | 435/7 |
| 4,851,356 | 7/1989 | Canfield | 436/510 |
| 5,324,667 | 6/1994 | Maci | 436/518 |
| 5,356,817 | 10/1994 | Cole | 436/64 |
| 5,501,988 | 3/1996 | Kobayoshi et al. | 436/548 |

OTHER PUBLICATIONS

Wehmann et al, *J. Endocr.*, vol. 117, No. 1, pp. 147–152, Apr. 1988.
Akar et al, *J. Clin. Endocrinol. Metab.*, vol. 66, No. 3, pp. 538–545, 1988.
Blithe et al, *Endocrinology*, vol. 122, No. 1, pp. 173–180, Jan. 1988.
Birken et al, *Endocrinology*, vol. 123, pp. 572–583, 1988.
Birken et al, *Endocrinology*, vol. 112, pp. 657–666, 1987.
Lefort et al, *Endocrinology*, vol. 119, pp. 924–931, 1986.
Wehmann et al, *Chemical Abstracts*, vol. 102, p. 72, Ref. #143383n, 1985 (Ann. Endocrinol. 1984, 45(4–5), 291–295).
Abstract Nos. B2.144.09, B2.144.10, 15th International Cancer Congress, Aug. 16–22, 1990.
Akar et al., *Clin. Endo. and Metab.* 66:538 (1988).
Alfthan et al., *Jo. Clin. Endocrin. & Metabolism* 70(3):783 (Mar. 1990).
Birken et al., *Endocrinology* 121(2):657 (1987).
Birken et al., *Endocrinology* 123(1):572 (1988).
Birken et al., *J. Biol. Chem.* 252:5386 (1977).
Blithe et al., *Endocrinology* 122(1):173 (1988).
Cole et al., *Cancer Research* 48:1356 (Mar. 1, 1988).
Greene et al., *Methods in Enzymology* XLVII:170 (1977).
Kardana et al., *British Journal of Cancer* 58 (3) (Sep. 1988).
Kohler et al., *Nature* 256:495 (1975).
Krichevsky et al., *Endocrinology* 123 (1):584 (1988).
O'Connor et al., *Cancer Research* 48:1361 (Mar. 1, 1988).
Ryan et al., *Recent Progress in Hormone Research* 43:83 (1987).
Shome et al., *J. Clin. Endo. and Metab.* 36:618 (1973).
Smyth, *Methods in Enzymology* 11:214 (1967).
Schroeder et al., *Clin. Chem.* 29(4):667 (1983).

*Primary Examiner*—Cecilia J. Tsang
*Assistant Examiner*—Abdel A. Mohamed
*Attorney, Agent, or Firm*—Townsend and Townsend and Crew

[57] ABSTRACT

The present invention relates to the purification of the human chorionic gonadotropin β-core molecule which can then be used as the antigen in the preparation of antibodies to the β-core molecule. The combination of the purified β-core molecule and the antibodies can be used in an immunoassay kit to measure β-core molecules in the presence of structurally similar molecules, i.e., hCG, LH, hCGβ-subunit and LHβ-subunit. Measurement of the β-core molecule is particularly useful in testing for pregnancy and many malignancies.

3 Claims, 13 Drawing Sheets

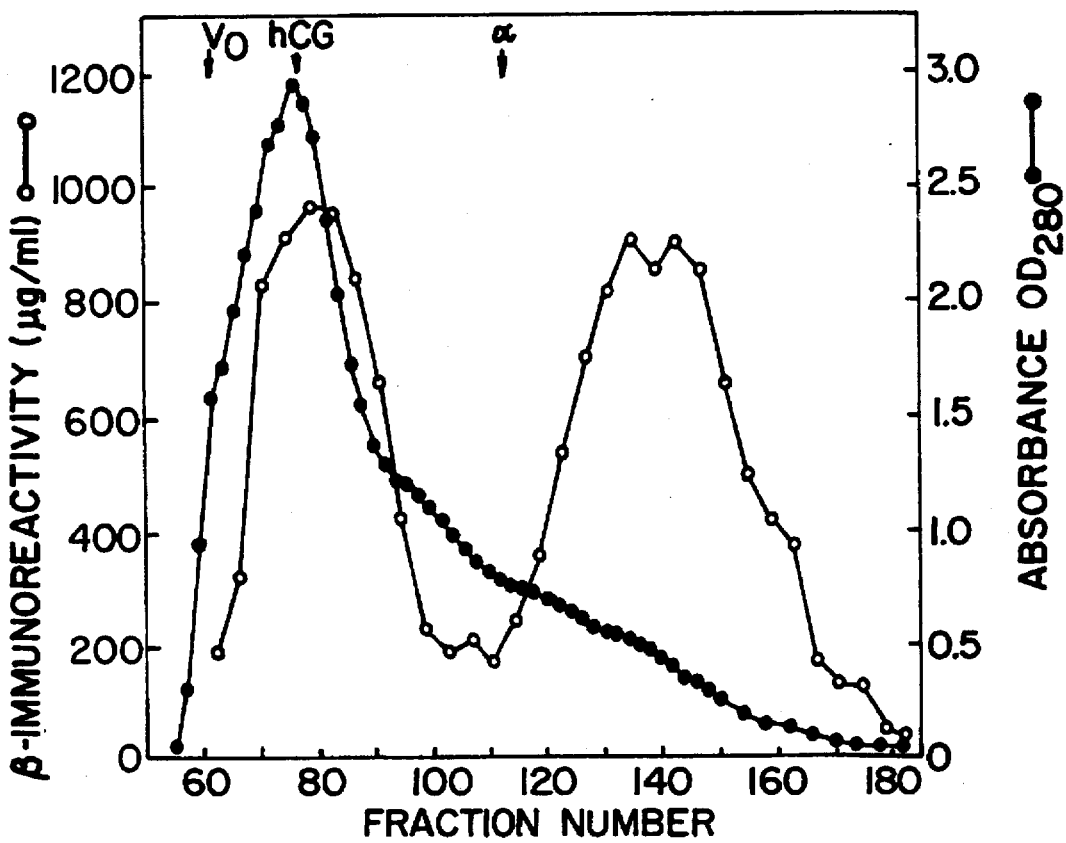
FIG. IA.
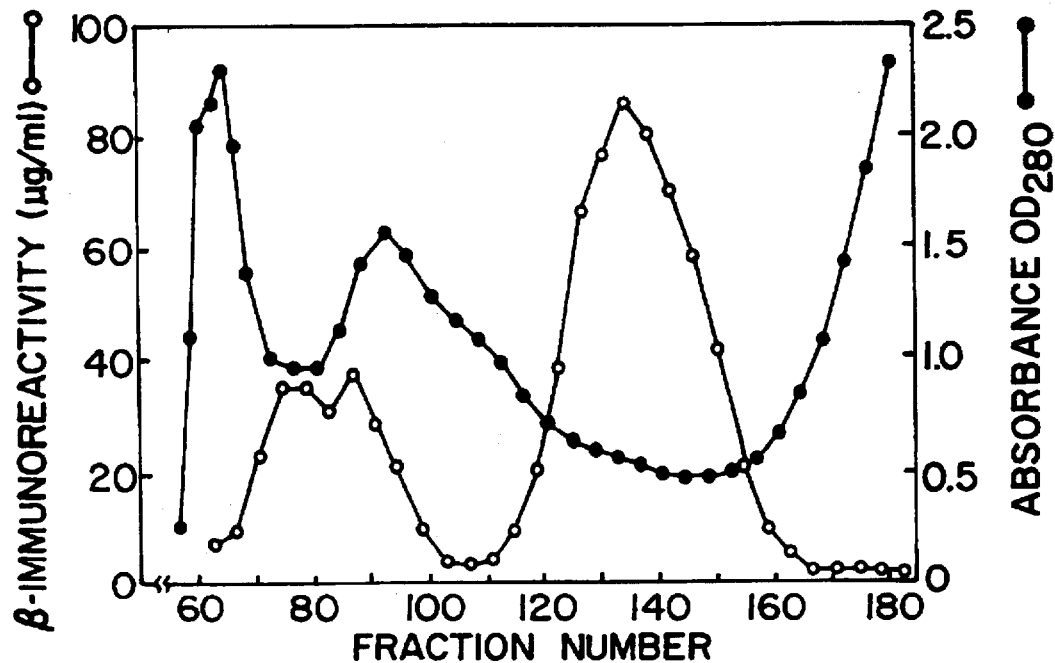
FIG. IB.

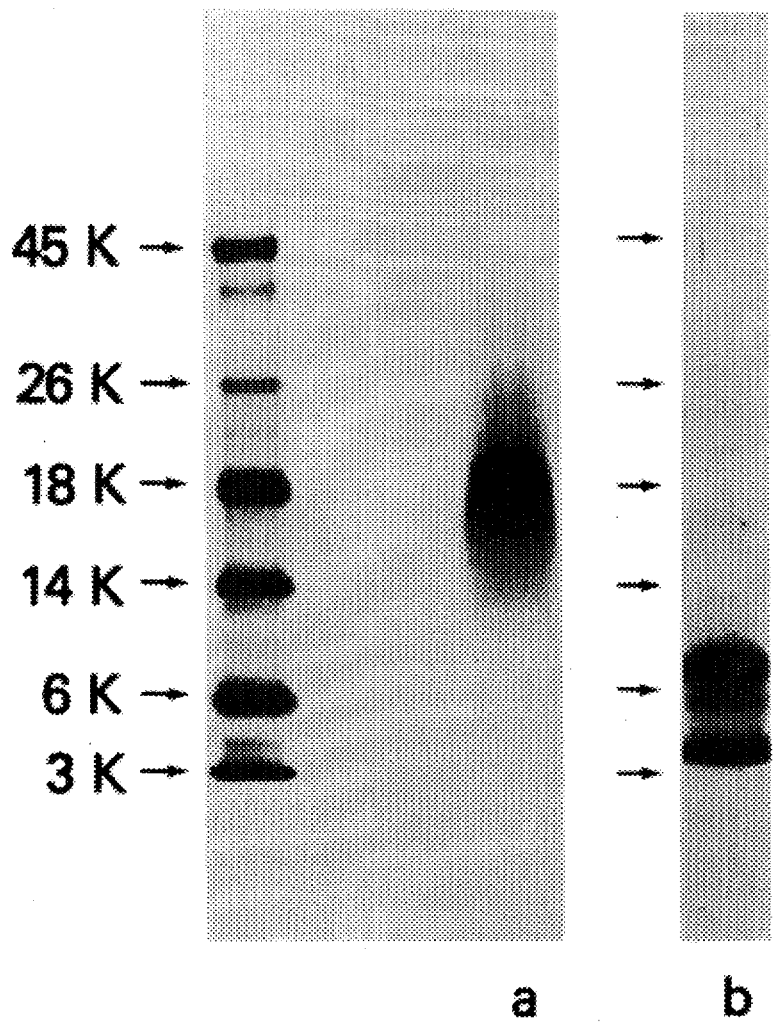
F I G. 4

NATURAL HUMAN CHORIONIC GONADOTROPIN β-CORE MOLECULE

This is a Division of application Ser. No. 07/789,835, filed Nov. 12, 1992, now U.S. Pat. No. 5,445,968, which is a Continuation-In-Part application of application Ser. No. 07/292,985, filed Jan. 3, 1989 (now abandoned).

BACKGROUND OF THE INVENTION

1. Field of the Invention

The present invention relates to a pure form of the human chorionic gonadotropin β-core molecule and the preparation of antibodies with specificity for the β-core molecule. The present invention also relates to an immunoassay kit comprising the purified β-core molecule and the antibodies, which kit can be used to measure β-core molecules in the presence of molecules which contain structural similarities.

2. Background Information

During pregnancy, large quantities of human chorionic gonadotropin (hCG) are produced. In addition to hCG, the urine of pregnant women contains free β-subunit, free α-subunit, and small mol wt forms of β-subunit known as β-core fragments (Franchimont P, et al, 1972, Polymorphism of protein and polypeptide hormones, Clin Endocrinol (Oxford) 1:315; Good A. et al, Molecular forms of human chorionic gonadotropin in serum, urine, and placental extracts, Fertil Steril 28:846; Taliadouros G S, et el, 1982, Biological and immunological characterization of crude commercial human choriogonadotropin, J Clin Endocrinol Metab 54:1002). The β-core fragments (termed β-core molecules herein) can account for as much as 70% of the total β-immunoreactivity in pregnancy urine (Schroeder H R et al, 1983, Specificity of human β-choriogonadotropin assays for the hormone and for an immunoreactive fragment present in urine during normal pregnancy, Clin Chem 29:667).

When hCGβ is injected into nonpregnant individuals, the β-core molecule is found as a metabolite in urine (Wehmann R E, et al, 1980, Characterization of a discrete degradation product of the human chorionic gonadotropin β-subunit in humans, J Clin Endocrinol Metab 51:101). The β-core molecule is also found in the urine of individuals with various forms of trophoblastic disease and malignancy (Papapetrou P D, et al, 1980, Ectopic production of human chorionic gonadotropin (hCG) by neoplasms, Cancer 45:2583; Hattori M, et al, 1980, Qualitative and quantitative analyses of human chorionic gonadotropin and its subunits produced by malignant tumors, Cancer 46:355; Masure H R, et al, 1981, Characterization of a small molecular size urinary immunoreactive human chorionic gonadotropin (hCG)-like substance produced by normal placenta and by hCG-secreting neoplasms, J Clin Endocrinol Metab 53:1014; Papapetrou P D, et al, 1986, The origin of a human chorionic gonadotropin β-subunit-core fragment excreted in the urine of patients with cancer, Acta Endocrinol (Copenhagen) 112:415). Papapetrou et al. (Papapetrou P D, et al, 1980, Ectopic production of human chorionic gonadotropin (hCG) by neoplasms, Cancer 45:2583) studied patients with nontrophoblastic malignant disease and found that while some of the patients had positive RIA hCGβ levels in both serum and urine, many of the patients were positive for RIA hCGβ only in the urine. The researchers analyzed some of these urine samples by gel filtration and found that the positive RIA hCGβ material eluted in the position of the β-core molecule; thus, in some patients, the β-core is the only hCG-related marker for malignancy.

Although the β-core molecule is of interest as both a normal metabolite of pregnancy and a marker for malignancy, little has been known about its structure and no pure β-core has been available to use as a standard. Furthermore, no methods have been available to specifically measure β-core in the presence of naturally occurring molecules with similarities in structure, i.e., hCG, LH, hCGβ-subunit or LHβ-subunit.

SUMMARY OF THE INVENTION

It is a general object of the present invention to provide a pure form of the chorionic gonadotropin β-core molecule.

It is another object of the present invention to provide a method of purifying the chorionic gonadotropin β-core molecule.

It is still another object of the present invention to provide antibodies to the chorionic gonadotropin β-core molecule.

It is another object of the present invention to provide an immunoassay for detecting the chorionic gonadotropin β-core molecule in a biological sample.

It is yet another object of the present invention to provide an immunoassay kit which can be used to measure the chorionic gonadotropin β-core molecule in the presence of molecules which contain structural similarities.

These and other objects, which will become apparent to those skilled in the art from the following detailed description, have been accomplished by the purification of the chorionic gonadotropin β-core molecule which can then be used as the antigen in the preparation of antibodies to the chorionic gonadotropin β-core molecule. The combination of the purified chorionic gonadotropin β-core molecule and the antibodies can be used in an immunoassay kit to measure chorionic gonadotropin β-core molecules in the presence of structurally similar molecules, i.e., hCG, LH, hCGβ-subunit, and LHβ-subunit. Measurement of the chorionic gonadotropin β-core molecule is particularly useful in testing for pregnancy and many malignancies.

BRIEF DESCRIPTION OF THE DRAWINGS

FIG. 1. Sephadex G-100 chromatography. Crude commercial hCG (upper panel) or acetone-precipitated material from pregnancy urine (lower panel) was subjected to gel filtration on a Sephadex G-100 column. The fractions were assayed for hCGβ immunoreactivity (O—O) and absorbance at 280 nm (●—●). $V_o$, Void volume.

FIG. 4. SDA-PAGE of P-core. P-Core was subjected to SDS-PAGE under nonreducing conditions (A) and in the presence of 5% mercaptoethanol (B).

DETAILED DESCRIPTION OF THE INVENTION

Figure 2A:
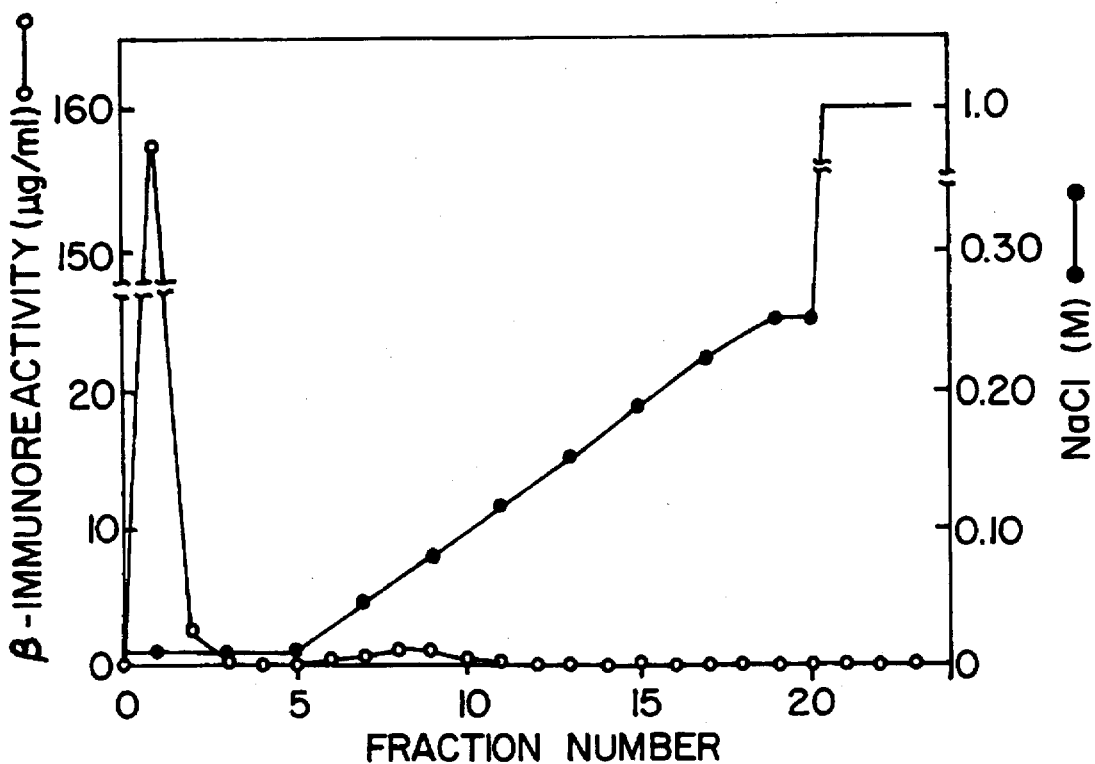
FIG. 2. DEAE-Sephacel chromatography of P-core and T-core. The Con A-bound forms of P-core were loaded onto DEAE-Sephacel columns that had been equilibrated with 10 mM ammonium acetate buffer, pH 7. The columns were eluted and the fractions were assayed for β-immunoreactivity using RIAs for P-core (upper panel) and T-core (lower panel). Ionic strength was measured by conductivity.

The present invention is directed to a pure form of the chorionic gonadotropin β-core molecule and its use as the antigen in the preparation of antibodies to the β-core molecule. It is implicit in the term "chorionic gonadotropin β-core molecule" that the subject of the present invention is the naturally occurring chorionic gonadotropin β-core molecule. The chorionic gonadotropin β-core molecule consists essentially of two polypeptide chains to which are linked two carbohydrate moities having the following structure

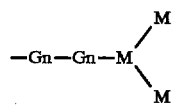

wherein Gn is N-acetylglucosamine, and M is mannose wherein one of the polypeptide chains has an amino acid sequence corresponding to amino acids 6–40 of human chorionic gonadotropin β subunit and the second of the polypeptide chains has an amino acid sequence corresponding to amino acids 55–92 of human chorionic gonadotropin β subunit.

In one embodiment of this invention, there is provided a method of purifying the chorionic gonadotropin β-core molecule from a biological sample, said method comprising the steps of:

(i) contacting the biological sample containing the β-core molecule with a carbohydrate-specific agent capable of binding at least one carbohydrate moiety present on the β-core molecule under conditions such that a complex is formed between the carbohydrate-specific agent and the β-core molecule;

(ii) removing material present in the sample not complexed with the carbohydrate specific agent;

(iii) dissociating the β-core molecule from the carbohydrate-specific agent so that a solution of β-core molecules is formed;

(iv) contacting the solution of β-core molecules with an agent capable of complexing negatively charged material present in the solution; and (v) separating the β-core molecules from the complexed material of step (iv) above. The biological sample is preferably urine, and most preferably human urine, although any sample-type can be used, such as tissue culture, amniotic fluid, etc.

In another embodiment, the method of purifying chorionic gonadotropin β-core molecule can further comprise the step of fractionating the components of the biological sample according to molecular weight, prior to subjecting that fraction of the biological sample containing components having a molecular weight in the range of about 5,000 to about 22,000 to steps (i)–(v) above.

According to another embodiment, the method of the invention further comprises the steps of: (a) fractionating the non-complexed material of step (v) above on the basis of molecular weight, which material includes the β-core molecules; and (b) collecting fractions containing β-core molecules.

Yet another embodiment provides for polyclonal antisera specific for chorionic gonadotropin β-core molecules (for example, RW25 and RW37; see Example 2 below). The polyclonal antisera of the present invention can have less than about a 0.5% cross-reactivity in terms of mass, and more preferably, less than about 0.2% cross-reactivity in terms of mass, with the β-subunit of chorionic gonadotropin.

In still another embodiment, the chorionic gonadotropin β-core molecule is used as the antigen in the preparation of monoclonal antibodies using the method of Köhler and Milstein, 1975, Nature 256:495.

Yet another embodiment is directed to a method of detecting chorionic gonadotropin β-core molecules in a biological sample comprising the steps of: (i) contacting the sample with polyclonal antiserum specific for the β-core molecule under conditions such that complexation between the β-core molecules and antibodies present in the antiserum occurs; and (ii) detecting the presence of the complex between the antibodies and the β-core molecules.

According to another embodiment, the combination of the purified β-core molecule and the antibodies to the β-core molecule are used in an immunoassay kit, for example, a radioimmunoassay kit or a colorimetric kit, etc., to measure β-core molecules in the presence of molecules which contain structural similarities, i.e., hCG, LH, hCGβ-subunit and LHβ-subunit. The assay is particularly advantageous in that it can detect extremely low levels of β-core in pregnancy or malignancy (for example, testicular cancer or other neoplasms) without false positive cross-reactivity with, for example, LH.

Yet another embodiment provides for a method of detecting chorionic gonadotropin β-core molecules in a biological sample comprising the steps of: (i) contacting said sample with an antibody specific for said β-core molecule under conditions such that complexation between said β-core molecules and said antibody occurs; and (ii) detecting the presence of said complex between said antibody and said β-core molecules. The antibody is preferably a monoclonal antibody, most preferably in pure form. The biological sample is preferably a human-derived body fluid, most preferably urine.

In still another embodiment, the present invention concerns a diagnostic kit for detecting the presence of chorionic gonadotropin β-core molecules in a biological sample comprising, in an immunologically effective amount, antibodies specific for chorionic gonadotropin β-core molecules and β-core molecules. The antibodies are preferably monoclonal antibodies. Preferably, the β-core molecules are labeled with a detectable label.

Still another embodiment is directed to a diagnostic kit for detecting the presence of chorionic gonadotropin β-core molecules in a biological sample comprising, in an immunologically effective amount, two sets of antibodies which bind remotely spaced epitopes on the β-core molecule, at least one of which is specific for the β-core molecule, and a means for insolubilizing the complex formed between the antibodies and the β-core molecules. Both sets of antibodies can be monoclonal antibodies, or one set can be polyclonal antibodies while the other set is monoclonal antibodies.

Yet another embodiment provides for monoclonal antibodies raised against and specific for human chorionic gonadotropin β-core molecules. The monoclonal antibodies are preferably labeled with a detectable label.

A further embodiment of the invention concerns a diagnostic kit for detecting the presence of chorionic gonadotropin β-core molecules in a biological sample comprising (i) two sets of antibodies which bind remotely spaced epitopes on the β-core molecule, at least one of which is specific for the β-core molecule, and (ii) a means for insolubilizing the complex formed between the antibodies and the β-core molecules, wherein a first set of antibodies is attached to a solid support and a second set of antibodies is labeled with a detectable label. Both sets of antibodies can be monoclonal antibodies, or one set can be polyclonal antibodies while the other set is monoclonal antibodies.

Another embodiment provides for polyclonal antibodies raised against and specific for human chorionic gonadotropin β-core molecules. The polyclonal antibodies are preferably labeled with a detectable label.

Development of the RW25 antiserum represents a major advance in the field of β-core measurement as this was the first antiserum developed that was capable of specific and sensitive detection of the β-core molecule. The RW37 antiserum, prepared using the identical materials and procedures as in the preparation of RW25 with the exception that a different New Zealand White female rabbit was used, represents a significant advancement over the achievements of RW25, as RW37 antisera has enhanced specificity with five-fold higher antibody titer and five to ten-fold greater sensitivity for β-core. In addition, the RW37 antisera is not significantly affected by various nonspecific matrix effects, thereby allowing measurement of larger volumes of biological samples and more accurate determination of both normal and abnormal levels of β-core molecules in the general population.

The present invention will be illustrated in detail in the following examples. These examples are included for illustrative purposes and should not be considered to limit the instant invention.

EXAMPLE 1

Purification of the β-Core Molecule from Pregnancy Urine

The β-core molecule was purified from pregnancy urine and from crude commercial hCG preparations, and the purified material was characterized with respect to size and carbohydrate content. To compare β-core carbohydrate to the carbohydrate of native hCGβ, a trypsin fragment of hCGβ was prepared which retains the β-core conformational immunological determinant recognized by the SB6 antiserum (Vaitukaitis J L, et al, 1972, A radioimmunoassay which specifically measures human chorionic gonadotropin in the presence of human luteinizing hormone, *Am J Obstet Gynecol* 113:751.), but has lost the carboxyl-terminal immunological determinant recognized by the R529 antiserum (Birken S, et al, 1982, Preparation and characterization of an improved β-COOH-terminal immunogen for generation of specific and sensitive antisera to human chorionic gonadotropin, *Endocrinology* 110:1555). This molecule, which was designated T-core (tryptic fragment of β-subunit), has been previously suggested to contain the N-linked oligosaccharides that are present in the amino-terminal portion of the molecule, but not the O-linked oligosaccharides of β-subunit that are associated with the carboxyl-terminal peptide portion of the molecule (CTP fragment) (Birken S, et al, 1987, Structural and functional studies of the tryptic core of the human chorionic gonadotropin β-subunit, *Endocrinology* 121:657). The present inventors have designated the β-core molecule(s) purified from pregnancy urine as P-core (pregnancy-related β-core) to distinguish it from T-core, the β-core prepared by trypsin digestion of hCGβ.

Materials and Methods

Sephadex G-100 and G-75 (superfine), Concanavalin-A (Con A)-Sepharose, DEAE-Sephacel, and Agarose-castor bean lectin-120 (Ricin-120) were obtained from Pharmacia Fine Chemicals (Uppsala, Sweden). Agarose-bound *Lens culinaris* agglutinin (lentil) and *Arachis hypogaea* (PNA) were obtained from E-Y Laboratories, Inc. (San Mateo, Calif.). Purified hCGβ (CR123) was provided by Drs. S. Birken and R. Canfield through the Center for Population Research.

Purification of P-core

P-Core was purified from material precipitated by acetone from pregnancy urine (Blithe D L, et al., 1986, Inhibition of follicle-stimulating hormone/diethylstilbestrol-stimulated ovarian growth by extracts of pregnancy urine, *Endocrinology* 119:2270) and from crude commercial hCG (Diosynth, Oss, Holland). Throughout the purification procedures, β-core was monitored using a RIA consisting of SB6 antiserum (Vaitukaitis J L, et al., 1972, A radioimmunoassay which specifically measures human chorionic gonadotropin in the presence of human luteinizing hormone, *Am J Obstet Gynecol* 113:751) and [$^{125}$I]hCGβ trace. The crude material was dissolved in 0.2M ammonium acetate and subjected to gel filtration chromatography on a sephadex G-100 column (2.5×100 cm). Fractions of 2.5 ml were collected and the mol wt range of 5,000–22,000 (fractions 120–175; FIG. 1) was combined. The pooled material was loaded onto a column (25-ml bed volume) of Con A-Sepharose (Kornfeld R, et al., 1975, Interaction of immunoglobulin glycopeptides with Concanavalin A. *J Biol Chem* 250:2614; Baenziger J U, et al., 1979, Structural determinants of Concanavalin A specificity for oligosaccharides, *J Biol Chem* 254:2400). The column was washed with 125 ml Con A buffer (0.2M ammonium acetate, pH 7; 1 mM $MgCl_2$; 1 mM $CaCl_2$; 1 mM $MnCl_2$; 0.5M NaCl; and 0.03% $NAN_3$), followed by elution with 115 ml Con A buffer containing 0.5M α-methyl-D-mannoside. The bound and nonbound fractions from the Con A column were dialyzed against 4 liters 0.05M ammonium acetate, pH 7, at 4° C. overnight. The fractions were lyophilized and processed separately in subsequent experiments. The Con A-bound material was redissolved in 5 mM ammonium acetate and loaded onto a DEAE-Sephacel column (5-ml bed volume). After washing the column with 10 mM ammonium acetate, the column was eluted with a linear salt gradient from 0–0.25M NaCl in 10 mM ammonium acetate, pH 7.

The DEAE-nonbound material was pooled and subjected to chromatography on Sephadex G-75 (superfine; 1.5×90 cm). The column was eluted with 0.2M ammonium acetate, and fractions of 1.2 ml were collected. Fractions 80–99 (see FIG. 3) were pooled, and this material was designated P-core and was used as both the standard and the trace (labeled with $^{125}I$) in subsequent RIAs using SB6 antiserum. The P-core material was iodinated with $^{125}I$ using the Iodo-Gen transfer method (Fraker P J, et al, 1978, Protein and cell membrane iodination with a sparingly soluble choloramide, 1,3,4,6-tetrachloro-3a,6a-diphenylglycouril, Biochem Biophys Res Commun 80:849) (SA, ~100 µCi/µg). The dose-response curve of P-core obtained using $[^{125}I]$P-core as the trace was linear. This is in contrast to the nonlinear (dog-leg) dose-response curve that was apparent when $[^{125}I]$hCGβ was used as the trace. Nonlinearity can result in underestimates of P-core concentration due to the inability of P-core to completely displace $[^{125}I]$hCGβ from SB6 antiserum.

Characterization of P-core:

P-Core was subjected to sodium dodecyl sulfate-polyacrylamide gel electrophoresis (SDS-PAGE) using 18% acrylamide slab gels containing 5% glycerol. The P-core material was electrophoresed under nonreducing conditions, in which mercaptoethanol was omitted from the sample buffer, and under reducing conditions (5% mercaptoethanol) (Laemmli U K, 1970, Cleavage of structural proteins during the assembly of the head of bacteriophage $T_4$, *Nature* (London) 227:680). The gels were stained with $AgNO_3$ (Oakley B R, et al., 1980, A simplified ultrasensitive silver stain for detecting proteins in polyacrylamide gels, *Anal Biochem* 105:361). Protein mol wt standards [3,000–45,000; obtained from BRL (Bethesda, Md.)] were used to calibrate the gels.

Sialic acid was released from P-core by hydrolysis in 0.1N $H_2SO_4$ for 90 min at 85° C. The extent of hydrolysis under these conditions was determined using N-acetylneuramin-lactose (Sigma Chemical Co., St. Louis, Mo.) as a standard. The amounts of sialic acid released by hydrolysis were measured by the thiobarbituric acid assay of Warren (Warren L, 1959, The thiobarbituric acid assay of sialic acids, *J Biol Chem* 234:1971). The protein concentration was determined by the method of Lowry et al. (Lowry O H, et al., 1951, Protein measurement with the Folin Phenol reagent, *J Biol Chem* 193:265).

Preparation of T-core from purified β-subunit:

Crude commercial hCG was subjected to chromatography on Sephadex G-100, as described above. The fractions containing β-immunoreactivity with a mol wt range of 40,000–80,000 were pooled. The β-subunit was dissociated from hCGα by incubation in 10M urea, pH 4.5, for 1 h at 37° C., followed by chromatography on DEAE-Sephacel in 8M urea. The purified β-subunit was eluted from the DEAE column with 0.5M NaCl, dialyzed, and lyophilized. hCGβ was subjected to trypsin, as described previously (Birken S, et al., 1986, Tryptic digestion of the α subunit of human choriogonadotropin, *J Biol Chem* 261:10719). Briefly, the purified β-subunit was dissolved in 0.1M $NH_4HCO_3$, pH 7.9. Trypsin (Worthington Diagnostic System, Inc., Freehold, N.J.) was dissolved at 10 mg/ml in 0.001N HCl, pH 2.9, and was added (1%, wt/wt) to the subunit preparation at 0 and 45 min of incubation. After a total of 90 min of incubation at 25° C., the material was frozen and lyophilized. After trypsin treatment of hCGβ, the T-core and CTP fragments of β-subunit were separated by chromatography on Con A-Sepharose. The T-core fragment bound to the Con A and was eluted with 0.5M α-methyl-D-mannoside in Con A buffer, dialyzed, and lyophilized. The T-core preparation was used as the standard preparation in subsequent RIAs for T-core using SB6 as antiserum and $^{125}I$-labeled hCGβ as trace.

Treatment of β-core fragments with neuraminidase:

Aliquots of purified P-core, T-core, and hCGβ (CR123) were incubated with insoluble neuraminidase (Sigma) in 0.5M sodium acetate, pH 5, for 16 h at 37° C. Control samples were incubated under the same conditions without enzyme. The insoluble neuraminidase was separated by centrifugation.

Lectin chromatography of β-fragments:

The purified P-core and T-core preparations were subjected to chromatography on a column (1.5-ml bed volume) of *Lens culinaris* agglutinin-agarose (Kornfeld K, et al., 1981, The carbohydrate-binding specificity of pea and lentil lectins, *J. Biol Chem* 256:6633). The unbound materials were eluted with 10 ml 0.2M ammonium acetate buffer, pH 7, containing 1 mM $MnCl_2$, 1 mM $CaCl_2$, 0.01% BSA, and 0.01% $NAN_3$. The bound materials were eluted with the same buffer containing 0.5M α-methyl-D-mannoside (10 ml). The fractions were dialyzed against 0.05M ammonium acetate for 16 h at 4° C. The amount of immunoreactivity in each fraction was determined by RIA for P-core or T-core, as appropriate.

The purified P- and T-core fragments (before and after neuraminidase treatment) were dissolved in PBS, pH 7.4, containing 0.1% BSA. The fragments were loaded onto columns of Ricin-120-agarose (Nicolson G L, et al., 1974, Characterization of two plant lectins from *Ricinus communis* and their quantitative interaction with a murine lymphoma, *Biochemistry* 13:196; Irimura T, et al., 1974, Carbohydrate-binding specificity of the so-called galactose-specific phytohemaglutinins, *Carbohydrate Res* 39:317) (1-ml bed volume). The unbound materials were eluted with 10 ml PBS containing 0.1% BSA. The bound materials were eluted with 10 ml lactose (100 mg/ml) in PBS-0.1% BSA. The amount of β-fragments in each fraction was determined by RIA.

P-Core, T-core, and hCGβ(CR123) (before and after neuraminidase treatment) were loaded onto columns (1-ml bed volume) of PNA-agarose (Lotan R, et al., 1975, The purification, composition, and specificity of the anti-T lectin from peanut (*Arachis hypogaea*), *J Biol Chem* 250:8518). The unbound materials were eluted with 6 ml PBS containing 1% BSA. The bound materials were eluted with 5 ml PBS containing 1% BSA and lactose (100 mg/ml). The amount of immunoreactivity in each fraction was determined by RIA.

RIA procedures:

To monitor P-core during purification, the present inventors used a RIA consisting of SB6 antiserum, $[^{125}I]$hCGβ trace, and hCGβ (CR123) standard. In the course of purifying P-core, it was noted that the P-core exhibited a dose-response curve that was not parallel to hCGβ and not linear on a logit-log plot. The dose-response curve had a dog-leg shape. Accordingly, after purifying P-core, the present inventors devised a RIA for P-core in which a linear dose-response curve for P-core was obtained. For this P-core RIA, [$^{125}$I]P-core was used as trace, purified P-core as standard, and SB6 antiserum. This P-core RIA was used in all the lectin studies involving P-core.

For the lectin studies involving T-core, there was devised a T-core RIA consisting of T-core standard, SB6 antiserum, and [$^{125}$I]hCGβ trace. T-Core exhibited a satisfactory dose-response curve in this system.

Purification and characterization of P-core:

Crude commercial hCG and acetone-precipitated material from pregnancy urine were subjected to chromatography on Sephadex G-100 (FIG. 1). Fractions 120–175 were pooled and designated P-core. This pool contained negligible hCGβ carboxyl-terminal peptide immunoreactivity (<0.5% of the SB6 immunoreactivity). The P-core preparations were subjected to chromatography on Con A-Sepharose. Most of the material bound to Con A (see Table 1 below).

TABLE 1

Con A-Sapharose Binding of P-core and T-core

| | % Con A-Nonbound | % Con A-Bound |
|---|---|---|
| P-Core (crude hCG) | 16 | 84 |
| P-Core (acetone-precipitated pregnancy urine) | 3 | 97 |
| T-Core (crude hCG) | 14 | 86 |

The P-core isolated directly from pregnancy urine had a higher percentage of Con A-bound material. Subsequent data refer to processing of the Con A-bound P-core material obtained from commercial hCG. However, processing of the Con A-nonbound fraction of P-core yielded similar results with respect to binding to DEAE and binding to Ricin-120 before and after neuraminidase treatment.

Figure 2B:
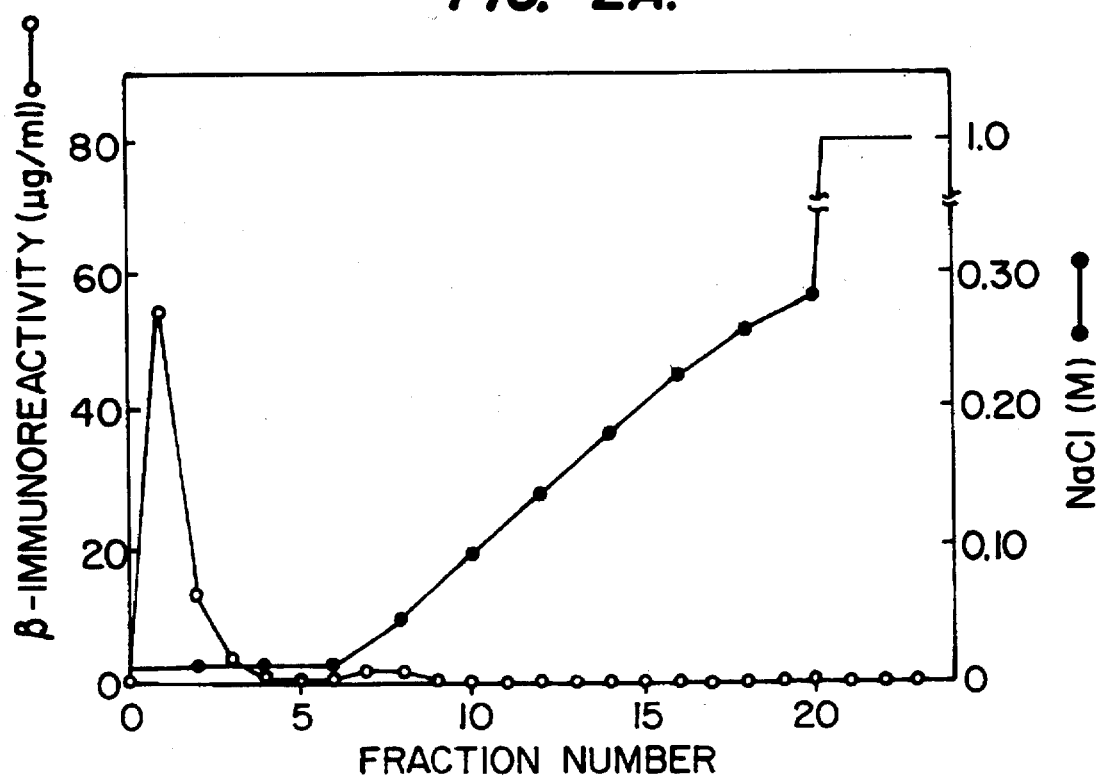
Figure 3:
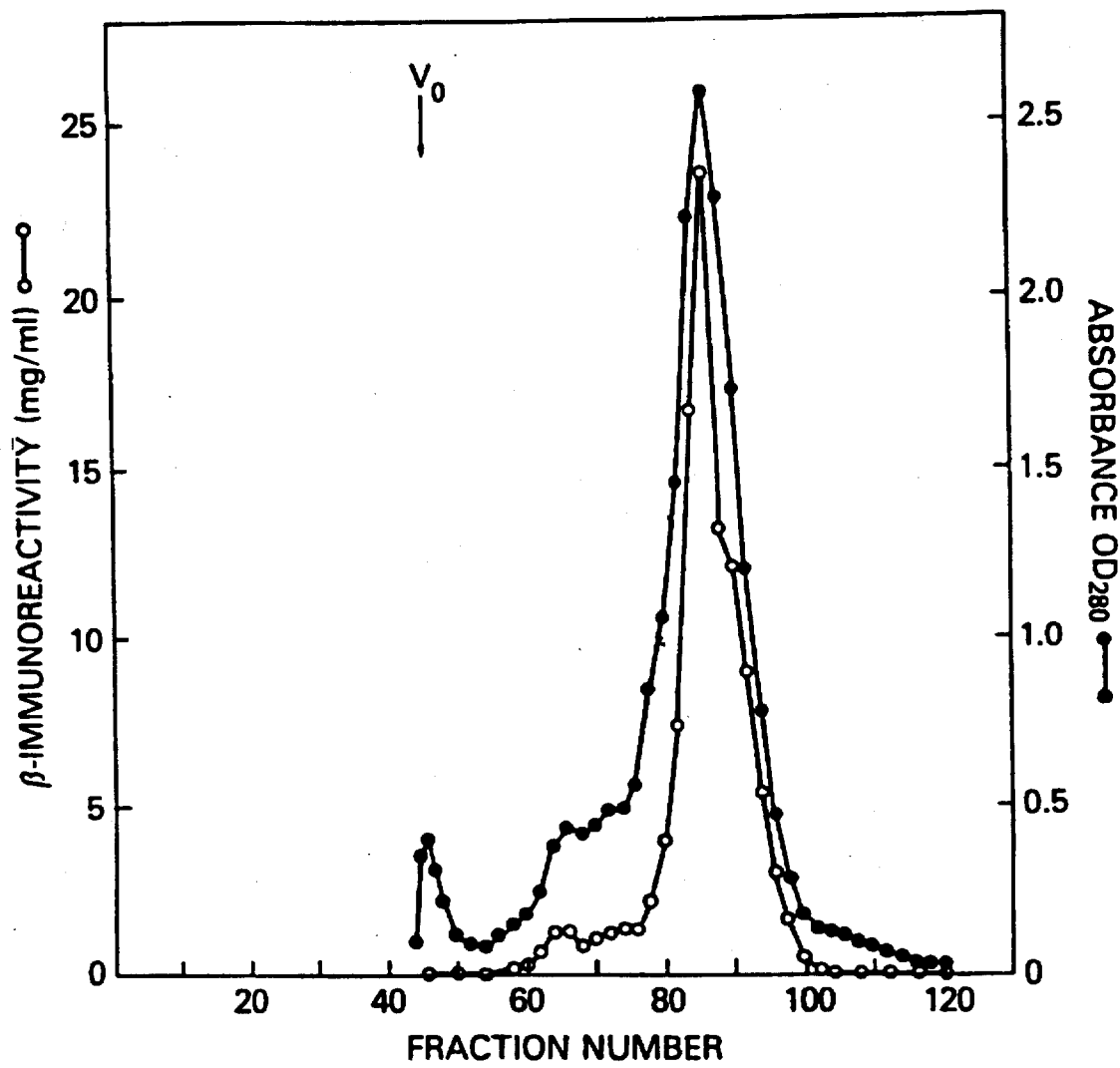
FIG. 3. Sephadex G-75 (superfine) chromatography of P-core. The Con A-bound and DEAE-purified P-core preparation was subjected to gel filtration on a column of Sephadex G-75 (superfine). The fractions were assayed for β-immunoreactivity (O—O) and for absorbance at 280 nm (●—●). $V_o$, Void volume.

The Con A-bound P-core preparation was chromatographed on DEAE-Sephacel using conditions under which intact hCGβ binds to DEAE. Surprisingly, more than 90% of the β-immunoreactivity was not retained by the resin (FIG. 2). The DEAE-nonbound fractions of P-core were further purified on Sephadex G-75 (superfine; FIG. 3). Fractions 80–99, containing the peak of β-immunoreactivity (mol wt range, 10,000–21,000) were pooled. The average apparent mol wt of the pool was 17,500. Fractions containing β-immunoreactivity with mol wt greater than 21,000 may represent aggregates of P-core or other fragments of β-subunit; this population of molecules was not studied further.

The purified P-core preparation was subjected to SDS-PAGE under nonreducing and reducing conditions (FIG. 4). In the absence of a reducing agent, P-core appeared to be a single broad band with an apparent mol wt of about 17,000 (FIG. 4a). After reduction of the disulfide bonds, SDS-PAGE of P-core resulted in three bands with apparent mol wt of 8,000, 6,000, and 3,500 (FIG. 4b).

Purified P-core was subjected to mild acid hydrolysis, and the sialic acid content of the material was measured. The sialic acid content of the P-core preparation was 0.2% (wt/wt) based on protein amounts determined by either the Lowry method (0.23%) or RIA (0.20%). If a mol wt of 10,000 was assumed for the polypeptide backbone (Birken S, et al., The structure of the hCG beta core fragment present in pregnancy urine. 68th Annual Meeting of The Endocrine Society, Anaheim, Calif., 1986, p. 159 (Abstract)) and two oligosaccharide chains of P-core, then the molar ratio of sialic acid to P-core would be less than 0.07 βmol sialic acid/βmol P-core.

Preparation of T-core:

The carbohydrate of the purified P-core material was compared with the native carbohydrate of an analogous region of hCGβ. hCGβ contains two asparagine-linked oligosaccharides on the amino-terminal portion of the molecule and four O-serine-linked oligosaccharides on the CTP portion (Kessler M J, et al., 1979, Structures of N-glycosidic carbohydrate units of human choriogonadotropin, *J Biol Chem* 254:7901; Kessler M J, et al., 1979, Structure and location of the O-glycosidic carbohydrate units of human chorionic gonadotropin, *J Biol Chem* 254:1909). Since P-core lacks the CTP-immunoreactive determinant and, accordingly, presumably lacks the bulk of the O-linked carbohydrate (see below) that is associated with the CTP portion of hCGβ, the present inventors prepared a trypsin fragment of hCGβ (T-core) that retained the β-core immunodeterminant associated with the aminoterminal portion of the molecule and was devoid of the CTP region (Birken S, et al., 1987, Structural and functional studies of the tryptic core of the human chorionic gonadotropin β-subunit, *Endocrinology* 121:657). To isolate T-core, fractions 80–110 from the Sephadex G-100 column (FIG. 1), corresponding to the elution positions of hCG and free β-subunit, were pooled and processed as described in Materials and Methods, above. The T-core fragment had an average apparent molecular size of 25,000 based on its elution position on Sephadex G-100. The T-core preparation bound to Con A (see Table 1) and did not bind to DEAE (FIG. 2, lower panel), similar to the behavior of P-core.

Lectin chromatography of P-core and T-core:

The carbohydrate natures of Con A-bound P-core and T-core preparations were examined by a variety of lectins with different carbohydrate-binding specificities (see Tables 2 and 3 below).

TABLE 2

Lectin Binding and T-core and P-core (Con A-bound)

| | T-Core (% bound) | | P-Core (% bound) | |
|---|---|---|---|---|
| Lectin (specificity) | Untreated | Neuraminidase-treated | Untreated | Neuraminidase-treated |
| *Lens culinaris* (M—Gn—Gn—Asn) M F | 87.0 | ND | 61.0 | ND |
| Ricin-120 (galactose) M | 3.4 | 93.5 | 0.7 | 0.4 |

Binding to PNA-Agarose
[Specificity = βGal(1-3)GalNAc]

| | Untreated (% bound) | Neuraminidase treated (% bound) |
|---|---|---|
| hCGβ | 1.6 | 98.3 |
| P-core | 0.4 | 0.5 |
| T-Core | 0.1 | 0.4 |

ND, Not done.

*Lens culinaris* agglutinin has a binding specificity similar to that of Con A, except that the *Lens culinaris* lectin requires a core fucose linked to the N-acetylglucosamine that is linked to the asparagine residue (Kornfeld K,.et al., 1981, The carbohydrate-binding specificity of pea and lentil lectins, *J Biol Chem* 256:6633). Such a structure has been proposed for at least one of the two N-linked carbohydrate moieties that are present on hCGβ (Kessler M J, et al., 1979, Structures of N-glycosidic carbohydrate units of human choriogonadotropin, *J Biol Chem* 254:7901; Endo Y, et al., 1979, Structures of the asparagine-linked sugar chains of human chorionic gonadotropin, *J Biochem* 85:669; Mizuochi T, et al., 1980, Different asparagine-linked sugar chains on the two polypeptide chains of human chorionic gonadotropin. *Biochem Biophys Res Commun* 97:772). Indeed, 87% of the T-core preparation was retained by the *Lens culinaris*-agarose, and 61% of the P-core preparation was retained.

*Ricinus communis*-agglutinin (Ricin-120) requires terminal galactose for binding (Nicolson G L, et al., 1974, Characterization of two plant lectins from *Ricinus communis* and their quantitative interaction with a murine lymphoma, *Biochemistry* 13:196; Irimura T, et al., 1974, Carbohydrate-binding specificity of the so-called galactose-specific phytohemagglutinins, *Carbohydrate Res* 39:317). Neither P-core nor T-core bound appreciably to Ricin-120agarose (see Table 2). However, after treatment with neuraminidase, 93.5% of the T-core preparation bound to Ricin, indicating that a terminal galactose residue(s) had been exposed as a result of the neuraminidase treatment. In striking contrast, P-core did not bind to Ricin either before or after neuraminidase treatment (see Table 2). This observation suggests that P-core, which has retained its Con A-binding site(s) and most of its fucose residues, contains no appreciable terminal galactose or sialic acid-galactose residues.

hCGβ contains four O-linked oligosaccharides on the CTP portion of the molecule (Kessler M J, et al., 1979, Structure and location of the O-glycosidic carbohydrate units of human chorionic gonadotropin, *J Biol Chem* 254:1909). The absence of the CTP immunodeterminant on the P-core and T-core molecules suggests the possibility that the O-linked carbohydrate structures are not present on these β-core fragments. To examine this possibility, P-core and T-core (before and after treatment with neuraminidase) were subjected to chromatography on *Arachis hypogaea* (PNA)-agarose. *Arachis hypogaea*-PNA has binding specificity for the β-Gal(1–3)GalNAc sequence (Lotan R, et al., 1975, The purification, composition, and specificity of the anti-T lectin from peanut *Arachis hypogaea*), *J Biol Chem* 250:8518), which is the core structure of the carbohydrate found in the CTP region of hCGβ after removal of the terminal sialic acid residues (Kessler M J, et al., 1979, Structure and location of the O-glycosidic carbohydrate units of human chorionic gonadotropin, *J Biol Chem* 254:1909). Before neuraminidase treatment, very little hCGβ, P-core, or T-core bound to PNA-agarose (see Table 3). After removal of sialic acid, nearly all of the hCGβ bound to PNA, while virtually none of the P-core or T-core material bound to the lectin.

Discussion:

The data presented above indicate that the β-core fragment (herein called P-core) that is abundantly present in pregnancy urine differs strikingly in a number of respects from the β-subunit of hCG. To study P-core, the present inventors first needed to purify the molecule and obtain a RIA that could reliably quantify the material. While P-core retains some of the immunological determinants that are recognized by the SB6 antiserum, the RIA using purified βsubunit as trace and standard produced nonparallel and nonlinear results. Therefore, RIA results obtained throughout the purification protocol ware interpreted qualitatively rather than quantitatively. Interestingly, T-core (which was prepared from hCGβ by trypsin treatment) did not exhibit nonparallelism or inearity in the SB6 assay using purified non hCGβ as trace and standard. After purification of P-core by chromatography on Sephadex G-100, Con A-Sepharose, DEAE-Sephacel, and Sephadex G75 (superfine), a linear dose-response curve on a logit-log plot was obtained using purified P-core (weighed from powder) to prepare the standard curve, [$^{125}$I]P-core as trace, and SB6 antiserum. Development of this linear RIA made it possible to reliably quantify the results of further characterization.

Based on gel filtration on Sephadex G75 (superfine), P-core has an apparent molecular size of 17,500. SDS-PAGE of P-core under nonreducing conditions resulted in a single broad band with an approximate mol wt of 17,000. In the presence of a reducing agent, SDS-PAGE of P-core resulted in three bands with mol wt of 8,000, 6,000, and 3,500. Since P-core ls glycosylated, molecular size estimates based on gel filtration and SDS-PAGE are likely to overestimate by a significant amount the actual mol wt.

Purified P-core was assayed chemically to determine sialic acid content (Warren L, 1959, The thiobarbituric acid assay of sialic acids, *J Biol Chem* 2.34:1971) and protein concentration (Lowry O H, et el., 1951, Protein measurement with the Folin Phenol reagent, *J Biol Chem* 193:265). The sialic acid content of P-core was 0.2% (wt/wt). Based on a mol wt approximation for P-core of 10,000, these results indicate that less than 7% of the P-core molecules contain one sialic acid residue. This conclusion was further supported by the lectin chromatography studies.

P-Core lacks the immunological determinants present on the CTP portion of hCGβ; less than 0.5% of the SB6 immunoreactivity of the Sephadex G-100 pool is found using the R529 antiserum (Birken S, et el., 1982, Preparation and characterization of an improved β-COOH-terminal immunogen for generation of specific and sensitive antisera to human chorionic gonadotropin, *Endocrinology* 110:1555) that was generated to the CTP portion of hCGβ. hCGβ has been reported to contain two asparagine-linked oligosaccharides on the amino-terminal portion of the molecule and four O-linked oligosaccharides on the carboxyl-terminal portion (Kessler M J, et al., 1979, Structures of R-glycosidic carbohydrate units of human choriogonadotropin, *J Biol Chem* 254:7901; Kessler M J, et el., 1979, Structure and location of the O-glycosidic carbohydrate units of human chorionic gonadotropin, *J Biol Chem* 254:1909). To compare the carbohydrate on P-core to an analogous segment of hCGβ, a trypsin fragment of hCGβ (herein called T-core) was prepared. T-core retains the β-core immunodeterminant (SB6) and lacks the CTP immunodeterminant (R529) and, presumably, the bulk of O-linked carbohydrates associated with the CTP region (Birken S, et el., 1987, Structural and functional studies of the tryptic core of the human chorionic gonadotropin β-subunit, *Endocrinology* 121:657).

The lectin-binding studies of P-core and T-core revealed some interesting similarities, as well as some striking differences, in their oligosaccharide structures. The lectin binding behavior of P-core and T-core on Con A and *Lens culinaris* indicates similarities between these two populations with respect to mannose structure. Most of the P-core and T-core immunoreactivity bound to Con A, although in the case of the commercial hCG preparations, some of the T-core (derived from hCGβ) and P-core components were unable to bind to the lectin. These Con Anonbinding populations were unable to bind to freshly prepared columns of Con A, indicating that lack of binding was not due to initial overload. This type of microheterogeneity has been observed previously with the oligosaccharides on the α-subunit of hCG (Blithe D L, et al., 1985, Variations in the oligosaccharides on free and combined α subunits of human choriogonadotropin in pregnancy, *Endocrinology* 117:2218; Blithe D L, et al., 1987, Similarity of the clearance rates of free α-subunit and α-subunit dissociated from intact human chorionic gonadotropin, despite differences in sialic acid contents, *Endocrinology* 121:1215), and the structural basis is unclear.

Chromatography of T-core and P-core on *Lens culinaris* lectin resulted in 87% and 61% binding, respectively. Thus, in addition to retaining the Con A-binding site, the P-core retained most of the core fucose present on hCGβ.

Neither P-core nor T-core bound appreciably to Ricin-120, suggesting that neither population contained oligosaccharide structures with terminal galactose residues. After treatment with neuraminidase, most of the T-core (93.5%) immunoreactivity bound to Ricin, while none of the P-core molecules could bind to the lectin. This result indicates that T-core contains oligosaccharide antennae that terminate in sialic acid-galactose, while P-core apparently does not. Thus, P-core, if derived from the metabolism of intact hCG or hCGβ, has undergone processing in which terminal sialic acid and galactose have been removed.

Neither P-core nor T-core bound to PNA-agarose after neuraminidase treatment. In contrast, 98.3% of the neuraminidase-treated hCGβ bound to PNA-agarose, thus P-core and T-core do not contain the O-linked oligosaccharides present on hCGβ.

Figures 5A, 5B:
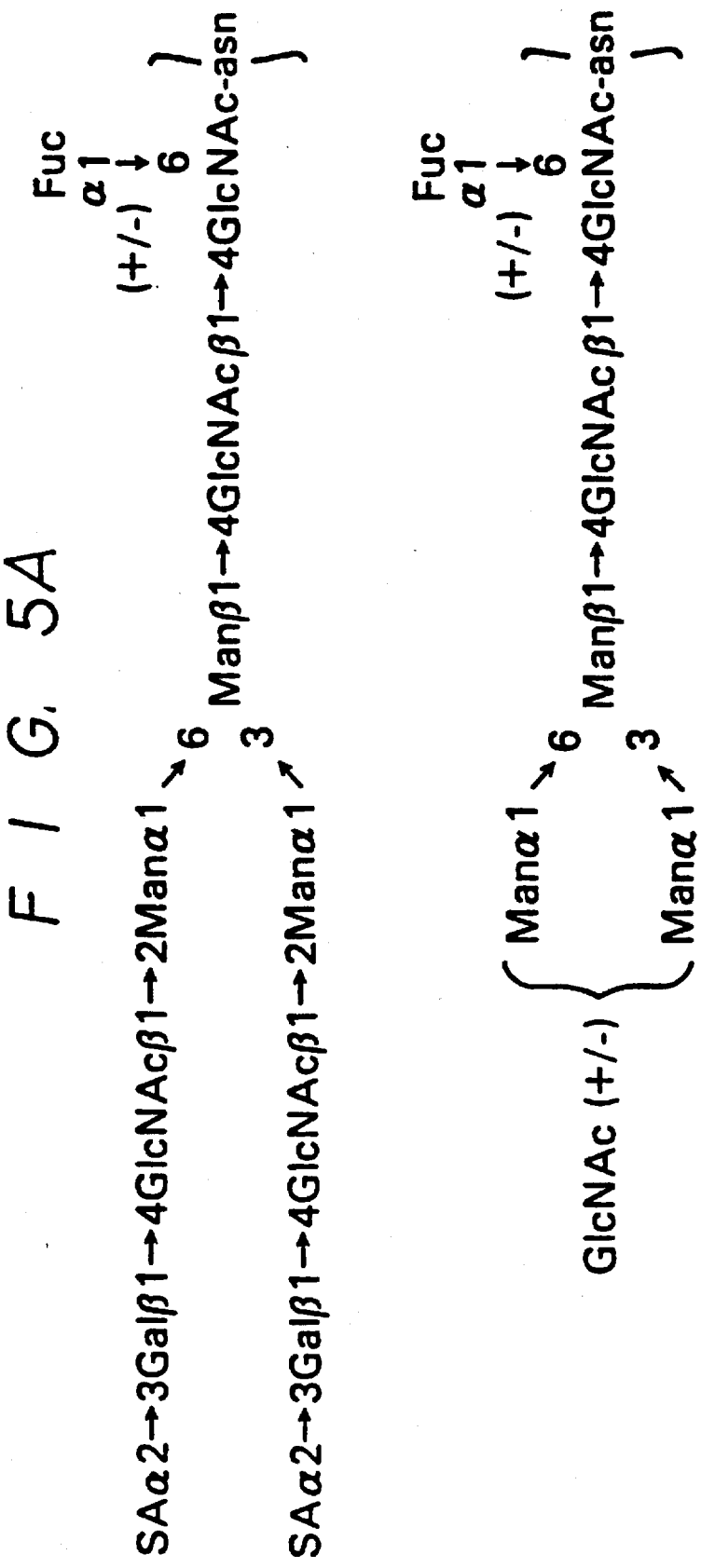
FIG. 5. Proposed oligosaccharide structures. The structure shown in FIG. 5A has been proposed previously (Kessler M J, et al, 1979, Structures of N-glycosidic carbohydrate units of human choriogonadotropin, J Biol Chem 254:7901; Endo Y, et al, 1979, Structures of the asparagine-linked sugar chains of human chorionic gonadotropin, J. Biochem 85:669; Mizuochi T, et al, 1980, Different asparagine-linked sugar chains on the two polypeptide chains of human chorionic gonadotropin, Biochem Biophys Res Commun 97:772) for the asparagine-linked sites of hCGβ. The present lectin binding data for T-core are consistent with this proposed structure. The structure shown in FIG. 5B is a hypothetical structure which is consistent with the present lectin binding data for P-core.

The carbohydrate portion of hCG has been analyzed by several groups (Kessler M J, et al., 1979, Structures of N-glycosidic carbohydrate units of human choriogonadotropin, *J Biol Chem* 254:7901; Kessler M J et al., 1979, Structure and location of the N-glycosidic carbohydrate units of human chorionic gonadotropin, *J Biol Chem* 254:1909; Endo Y, et al., 1979, Structures of the asparagine-linked sugar chains of human chorionic gonadotropin, *J Biochem* 85:669; Mizuochi T, et al., 1980, Different asparagine-linked sugar chains on the two polypeptide chains of human chorionic gonadotropin, *Biochem Biophys Res Commun* 97:772), and the structure proposed for the two N-linked glycosylation sites on the hCGβ subunit is a biantennary oliogosaccharide that is capable of binding to Con A (FIG. 5A). The present studies of T-core are generally consistent with this being the predominant structure. In contrast, the present lectin binding data for P-core are consistent with the presence of the structure(s) shown in FIG. 5B. The mechanism for production of this P-core carbohydrate structure is not fully clear. It is interesting to note that although hCG and its free β- and α-subunits as well as P-core are all isolated from pregnancy urine, P-core contains Con A-binding oligosaccharides that are virtually devoid of sialic acid and galactose, while hCG, free β, add free α appear in the urine with intact sialic acid-galactose-containing antennae (Kessler M J, et al., 1979, Structures of N-glycosidic carbohydrate units of human choriogonadotropin, *J Biol Chem* 254:7901; Kessler M J, et al., 1979, Structure and location of the O-glycosidic carbohydrate units of human chorionic gonadotropin, *J Biol Chem* 254:1909; Endo Y, et al., 1979, Structures of the asparagine-linked sugar chains of human chorionic gonadotropin, *J Biochem* 85:669; Mizuochi T, et al., 1980, Different asparagine-linked sugar chains on the two polypeptide chains of human chorionic gonadotropin, *Biochem Biophys Res Commun* 97:772; Blithe D L, et al., 1985, Variations in the oligosaccharides on free and combined α subunits of human choriogonadotropin in pregnancy, *Endocrinology* 117:2218; Blithe D L, et al., 1987, Similarity of the clearance rates of free α-subunit and α-subunit dissociated from intact human chorionic gonadotropin, despite differences in sialic acid contents, *Endocrinology* 121:1215).

Collectively, the available data do not rule out the possibility that P-core is a synthetic product containing a high mannose Con A-binding structure. A small amount of a β-core fragment has been observed in placental extracts (Good A, et al., 1977, Molecular forms of human chorionic gonadotropin in serum, urine, and placental extract, *Fertil Steril* 28:846) and tumor extracts (Hattori M, et al., 1980, Qualitative and quantitative analyses of human chorionic gonadotropin and its subunits produced by malignant tumors, *Cancer* 46:355), prompting speculation that a β-core molecule might be a secretory product (Masure H R, et al., 1981, Characterization of a small molecular size urinary immunoreactive human chorionic gonadotropin (hCG)-like substance produced by normal placenta and by hCG-secreting neoplasms, *J Clin Endocrinol Metab* 53:1014). However, Papapetrou and Nicopoulou [Papapetrou P D, et al., 1986, The origin of a human chorionic gonadotropin β-subunit-core fragment excreted in the urine of patients with cancer, *Acta Endocrinol* (Copenhagen) 112:415] were unable to find β-core fragments in tumor extracts from patients with large amounts of urinary β-core fragments. In addition, β-core has not been observed in the serum of either pregnant women or patients with hCG-secreting tumors, while as much as 85% of the total immunoreactive urinary hCG was β-core fragment [Franchimont P, et al., 1972, Polymorphism of protein and polypeptide hormones, *Clin Endocrinol* (Oxford) 1:315; Good A, et al., 1977, Molecular forms of human chorionic gonadotropin in serum, urine, and placental extracts, *Fertil Steril* 28:846; Schroeder H R, et al., 1983, Specificity of human β-choriogonadotropin assays for the hormone and for an immunoreactive fragment present in urine during normal pregnancy, *Clin Chem* 29:667; Wehmann R E, et al., 1980, Characterization of a discrete degradation product of the human chorionic gonadotropin β-subunit in humans, *J Clin Endocrinol Metab* 51:101; Papapetrou P D, et al., 1980, Ectopic production of human chorionic gonadotropin (hCG) by neoplasms, *Cancer* 45:2583; Hattori M, et al., 1980, Qualitative and quantitative analyses of human chorionic gonadotropin and its subunits produced by malignant tumors, *Cancer* 46:355; Masure H R, et al., 1981, Characterization of a small molecular size urinary immunoreactive human chorionic gonadotropin (hCG)-like substance produced by normal placenta and by hCG-secreting neoplasms, *J Clin Endocrinol Metab* 53:1014; Papapetrou P D, et al., 1986, The origin of a human chorionic gonadotropin β-subunit-core fragment excreted in the urine of patients with cancer, *Acta Endocrinol* (Copenhagen) 112:415; Vaitukaitis J L, 1973, Immunologic and physical characterization of human chorionic gonadotropin secreted by tumors, *J Clin Endocrinol Metab* 37:505]. Studies in rats have demonstrated the production of β-core fragments in kidney tissue and the excretion of fragments of hCGβ in rat urine after injection of hCG and hCGβ (Lefort G P, et al., 1986, Renal metabolism of the β-subunit of human choriogonadotropin in the rat, *Endocrinology* 119:924). In this light, it is tempting to speculate that the P-core in pregnancy urine may be a product of the metabolism of hCG and hCGβ in kidney. β-core fragments have been documented in the urine of normal subjects infused with hCG (Webmann R E, et al., 1981, Metabolic and renal clearance rates of purified human chorionic gonadotropin, *J Clin Invest* 68:184) or hCGβ (Wehmann R E, et al., 1980, Characterization of a discrete degradation product of the human chorionic gonadotropin β-subunit in humans, *J Clin Endocrinol Metab* 51:101), clearly confirming that degradative pathways for the production of urinary β-core fragments exist in humans. The fact that there are no measurable β-core fragments in pregnancy serum [Franchimont P, et al., 1972, Polymorphism of protein and polypeptide hormones, *Clin Endocrinol* (Oxford) 1:315; Good A, et al., 1977, Molecular forms of human chorionic gonadotropin in serum, urine, and placental extracts, *Fertil Steril* 28:846] suggests, but does not prove, that metabolism of hCGβ in renal parenchyma is the source of these molecules in pregnancy urine.

EXAMPLE 2

Preparation of Polyclonal Antisera with Specificity for hCG β-Core

1. Preparation of the Polyclonal Antiserum RW25

Materials:

Sephadex G-75 (superfine), Sephadex G-100, DEAE-Sephacel, and Concanavalin-A-Sepharose were obtained from Pharmacia Fine Chemicals (Piscataway, N.J.). Crude commercial HCG was purchased from Diosynth (Oss, Holland). α-methyl-D-mannoside (grade III) was obtained from Sigma Chemical Co. (St. Louis, Mo.). Highly purified (CR125) hCG, hCGα, and hCGβ were obtained from the Center for Population Research, NICHHD, NIH (Bethesda, Md.); these glycoprotein preparations were similar to the earlier preparations, CR119 and CR121, which were extensively characterized in previous reports (Wehmann R E, et al., 1981, The metabolic and renal clearance rates of purified human chorionic gonadotropin, *J Clin Invest* 68:194; Wehmann R E, et al., 1979, Metabolic clearance rates of the subunits of human chorionic gonadotropin in man, *J Clin Endocrinol Metab* 48:753; Canfield R E, et al., 1976, A new reference preparation of human chorionic gonadotropin and its subunits, *Bull WHO* 54:463). Highly purified hLH (NIDDK hLH I-3; RIA potency, $10 \times 10^6$ IU/g; WHO International Standard FSH/LH 70/45), hFSH (NIDDK hFSH I-3; RIA potency, $6.887 \times 10^6$ IU/g WHO International Standard FSH/LH 70/45), and hTSH (NIDDK hTSH I-6; RIA potency, $6.6 \times 10^3$ IU/g WHO hTSH International Standard 68/38) were gifts from the National Hormone and Pituitary Program, NIDDK (Baltimore, Md.).

Preparation of hCGβ-core:

A β-core preparation was purified from crude commercial hCG, as described by Blithe et al. (Blithe D L, et al., 1988, Purification of β-core fragment from pregnancy urine and demonstration that its carbohydrate moieties differ from those of native human chorionic gonadotropin-β, *Endocrinology* 122:173). Crude hCG was chromatographed on a Sephadex G-100 column (92.5×2.5 cm) using 0.2 mol/L ammonium acetate, pH 7, as the elution buffer. Fractions (2.5 mL) were assayed for hCGβ immunoreactivity (SB6 antiserum) and hCGα immunoreactivity (SA7 antiserum) (Wehmann R E, et al., 1981, Convenient radioimmunoassay for urinary human choriogonadotropin without interference by urinary human lutropin, *Clin Chem* 27:1997). Fractions with hCGβ immunoreactivity that eluted with an apparent molecular size of 5,000–22,000 were pooled and lyophilized. The pool was chromatographed on Concanavalin-A-Sepharose, the material that bound was eluted with 0.5 mol/L α-methyl-D-mannoside, and the eluted fractions were dialyzed against 0.05 mol/L ammonium acetate, pH 7, and lyophilized. This material was applied to a DEAE-Sephacel column; 98% of the β-core immunoreactive material was not retained by the DEAE resin, and this material was pooled and lyophilized. The material was further purified by gel filtration on Sephadex G-75 (superfine). Fractions with hCGβ immunoreactivity were pooled and lyophilized. This purified β-core preparation (apparent molecular size: 17,000) was used as the immunogen, the reference standard, and, when radioiodinated, the radioligand for the RIA (see below).

Immunization of rabbits:

Six New Zealand White female rabbits (4–6 kg) were immunized with purified β-core using a multiple site injection technique (Vaitukaitis J, et al., 1971, A method for producing specific antisera with small doses of immunogen. *J Clin Endocrinol Metab* 33:988). The primary immunization was with 50 μg β-core fragment in complete Freund's adjuvant; booster injections of 25 μg in incomplete Freund's adjuvant were given at 30, 60, and 120 days. The animals were bled at 7- to 14-day intervals, and serum was separated and stored frozen at −20° C. Serial dilutions of each antiserum were tested for their ability to bind $^{125}$I-labeled β-core, with minimal binding of $^{125}$I-labeled β-subunit.

RIA procedures:

For the RIA of β-core molecules, the present inventors prepared a pool of serum from animal RW25 obtained at different times and used purified β-core as the reference preparation and for iodination, which was performed using the Iodo-Bead (Pierce Chemical Co., Rockford, Ill.) method (Markwell MAK, 1982, A new solid state reagent to iodinate proteins. I. Conditions for the efficient labelling of antiserum, *Anal Biochem* 125:427; Fraker P J, et al., 1978, Protein and cell membrane iodination with a sparingly soluble chloroamide, 1,3,4,6-tetrachloro-3a,6a-diphenylglycouril, *Biochem Biophys Res Commun* 80:849). The specific activity of the product ranged from 70–130 Ci/g. The assay incubation volume was 0.6 mL; separation of free from antibody-bound radioligand was achieved by second antibody precipitation. All assays were done in duplicate.

To assay hCG immunoreactivity, the present inventors used the antiserum SB6 [which is directed against conformational determinants of the β-subunit (Vaitukaitis J L, et al., 1972, A radioimmunoassay which specifically measures human chorionic gonadotropin in the presence of human luteinizing hormone, *Am J Obstet Gynecol* 113:751) present on β-core molecules], purified hCG (CR123) as the reference preparation, and [$^{125}$I]hCG as the radioligand (Webmann R E, et al., 1981, The metabolic and renal clearance rates of purified human chorionic gonadotropin, *J Clin Invest* 68:194). In this system, β-core had a dose-inhibition curve parallel to that of hCG. RIAs for hCGβ and hCGα were performed as described previously (Wehmann R E, et al., 1979, Metabolic clearance rates of the subunits of human chorionic gonadotropin in man, *J Clin Endocrinol Metab* 48:753).

Human subjects' urine:

Urine samples were collected from 123 subjects: 28 normal men (aged 14–58 years), 28 normal premenopausal women (aged 19–32 years), 6 boys (aged 15 days to 9 years), 41 postmenopausal women (aged 48–66 years), 14 pregnant women (aged 23–31 years), 5 men with testicular cancer, and 1 man with a hepatoma. The duration of the pregnancies ranged from 6–32 weeks; the postmenopausal women all had very low serum estrogen levels and elevated serum gonadotropin concentrations. The urine samples were frozen at −20° C. until assayed.

Gel chromatography:

Gel chromatography of purified preparations of hCG, hCGα, and hCGβ was performed by applying the matarial in a volume of 2 mL to a 90×1.6 cm Sephadex G-100 column and eluting with 0.2 mol/L ammonium acetate buffer, pH 7. The flow rate was adjusted to 15 mL/h, and fractions of 2.5 mL were collected into tubes that contained 0.1 mL phosphate-buffered saline (PBS; 0.15 mol/L NaCl and 0.01 mol/L phosphate, pH 7.4) with 20 g/L BSA.

Gel chromatography of the urine from pregnant women was performed by applying 2 mL urine to a 92.5×1.6 cm Sephadex G-100 column and eluting with 0.2 mol/L ammonium acetate, pH 7. The flow rate was adjusted to 15 mL/h, and fractions of 2 mL were collected into tubes that contained 0.1 mL PBS with 20 g/L BSA.

Calculations:

Dose-inhibition curves and potency estimates in the various RIAs were analyzed by the logit-log program of Rodbard (Rodbard D, 1974, Statistical quality control and routine data processing for radioimmunoassays and immunoradiometric assays, *Clin Chem* 20:1255). Group comparisons were made by Student's t test (Snedecor G W, et al., 1957, Statistical Methods, Iowa State University Press, Ames), because the distribution of values in each group was normal when tested according to the method of Shapiro and Wilk (Shapiro S S, et al., 1965, An analysis of variance test for normality (complete samples), *Biometrika* 52:611). Linear regressions were analyzed by the least squares method (Snedecor G W, et al., 1957, Statistical Methods, Iowa State University Press, Ames) or by the method of York (York D, 1968, Least squares fitting of a straight line with correlated errors, *Earth Planetary Sci Lett* 5:320).

Antiserum production:

All six rabbits immunized with purified β-core produced antisera that reacted with iodinated β-core. Most of these antisera extensively bound labeled hCGβ as well. However, serum from one rabbit (RW25) had a considerably higher titer for binding β-core radioligand than for hCGβ radioligand (25% vs. 3%, at a 1:15,000 dilution of antiserum). This antiserum also had the greatest ability to discriminate β-core relative to hCG, β-subunit, and hLH in preliminary evaluation. Based on these observations, the present inventors prepared a pool of successive bleeds from this rabbit to use for the experiments described herein. A final titer of 1:12,000 of this pooled RW25 antiserum in an assay reaction volume of 0.6 mL resulted in 20–30% binding of the $^{125}$I-labeled β-core. The addition of unlabeled β-core resulted in displacement of antibody-bound radioligand at a dose of about 0.05 ng/tube; the $ED_{50}$ for β-core diluted in assay buffer was 1.2 ng/tube.

Figure 6:
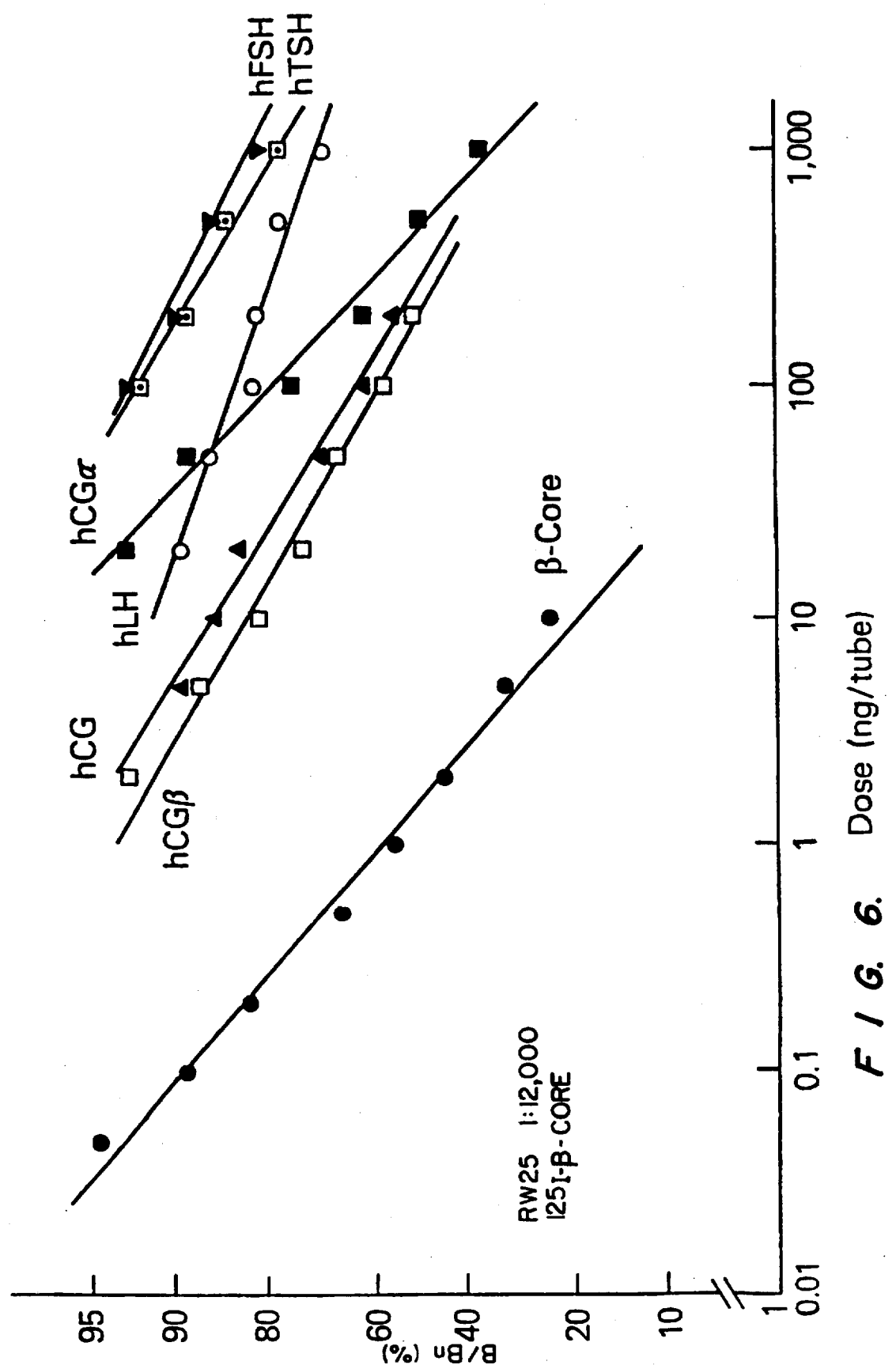
FIG. 6. Dose-response curves of various substances in the β-core RIA. Binding of radioligand as a percentage of binding at zero dose (B/B$_o$) in buffer is shown on the vertical axis; the dose is given on the horizontal axis.

Specificity:

Specificity was first evaluated by determining the cross-reactivities of various glycoprotein preparations in the β-core assay. Purified hFSH, hTSH, and hLH showed very low cross-reactivity in the β-core RIA; the ratios of estimated $ED_{50}$ for β-core and these test substances were $5 \times 10^{-5}$, $1.5 \times 10^{-4}$, and $9 \times 10^{-5}$ (wt/wt), respectively (FIG. 6). The cross-reactivities of purified (CR125), hCG, hCGβ, and hCGα preparations relative to purified β-core were $1.9 \times 10^{-3}$, $2.2 \times 10^{-3}$, and $7.0 \times 10^{-4}$ (wt/wt), respectively.

Figure 7:
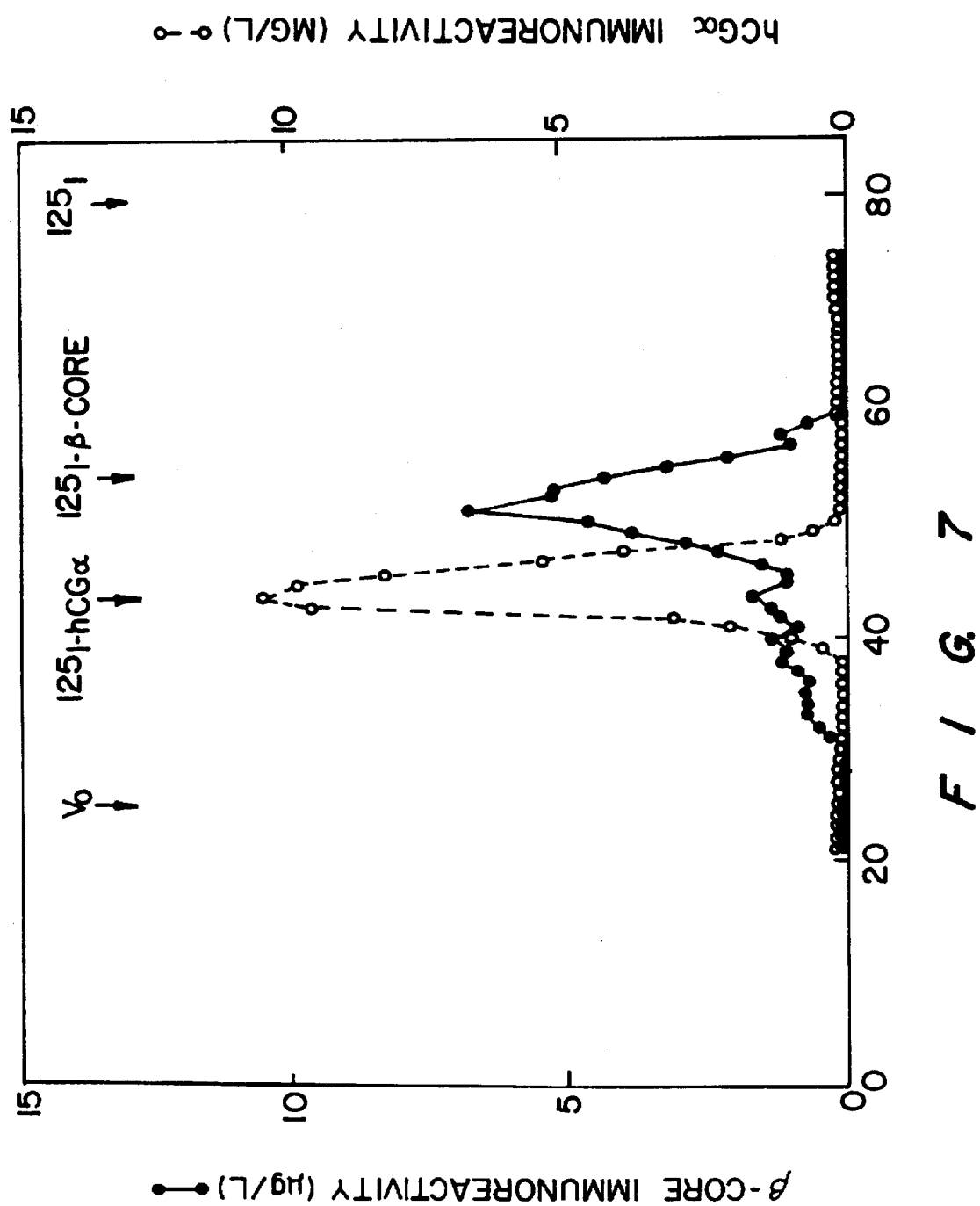
FIG. 7. Sephadex G-100 chromatography of purified hCGα CR125. Approximately 25 µg subunit were applied to a Sephadex G-100 column in a volume of 2.0 mL and eluted with 0.2 mol/L ammonium acetate buffer, pH 7. Fractions (2.5 mL) were collected in tubes that contained 0.1 mL PBS, 20 g/L BSA. Each fraction was assayed for β-core immunoreactivity (●) and hCGα immunoreactivity (O). The elution positions of the column markers are indicated by the arrows. V$_o$, Void volume.

The apparent cross-reactivity of the hCGα preparation in the β-core RIA was unexpected, since immunization with a derivative of hCGβ should not give rise to antibodies that react with epitopes on hCGα. Therefore, the immunoreactive forms in the hCGα preparation were characterized by gel chromatography on Sephadex G-100. The β-core immunoreactivity in the hCGα (CR125) subunit preparation was composed principally of contaminating β-core molecules, which eluted in a position separate from that of hCGα and coincident with the position of purified β-core (FIG. 7). The finding of β-core contamination of the hCGα (CR125) preparation prompted the examination of the hCG preparation from which the hCGα was derived. Indeed, the hCG (CR125) preparation was also contaminated with β-core fragments, in addition to possessing some apparent cross-reactivity intrinsic to the hCG molecule. In contrast, virtually all of the cross-reactivity in the hCGβ (CR125) preparation coeluted in the position of authentic β-subunit, suggesting that the β-subunit molecule itself has intrinsic cross-reactivity, and that its purified preparation contains negligible amounts of β-core contaminants. Based on the levels of immunoreactivity in the peaks after Sephadex G-100 chromatography, the revised estimates of the cross-reactivities of hCG and hCGα in the β-core RIA relative to purified β-core were $2 \times 10^{-3}$ and $3 \times 10^{-4}$ (wt/wt), respectively.

Figure 8:
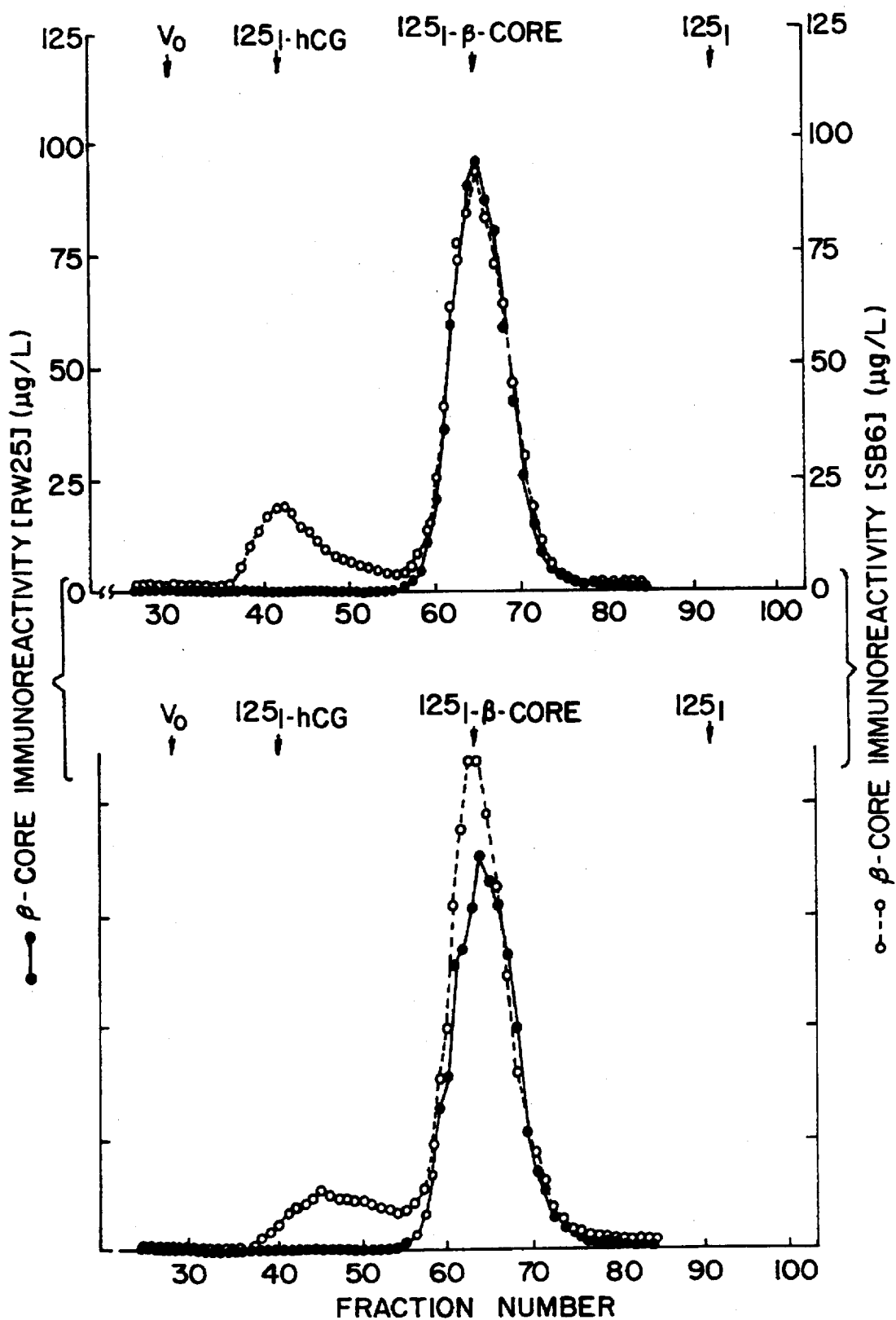
FIG. 8. Sephadex G-100 gel filtration of urine from two pregnant women. Two milliliters of urine were applied to the Sephadex G-100 column and eluted with 0.2 mol/L ammonium acetate buffer, pH 7. The fractions (2.0 mL) were collected in tubes that contained 0.1 mL PBS and 20 g/L BSA. Aliquots of each fraction were analyzed in the RIA for β-core (●) and in the RIA for hCG (O). The elution positions of the column markers are indicated by the arrows (the elution position of hCGβ is approximately fractions 44–48). V$_o$, Void volume.
Figure 9:
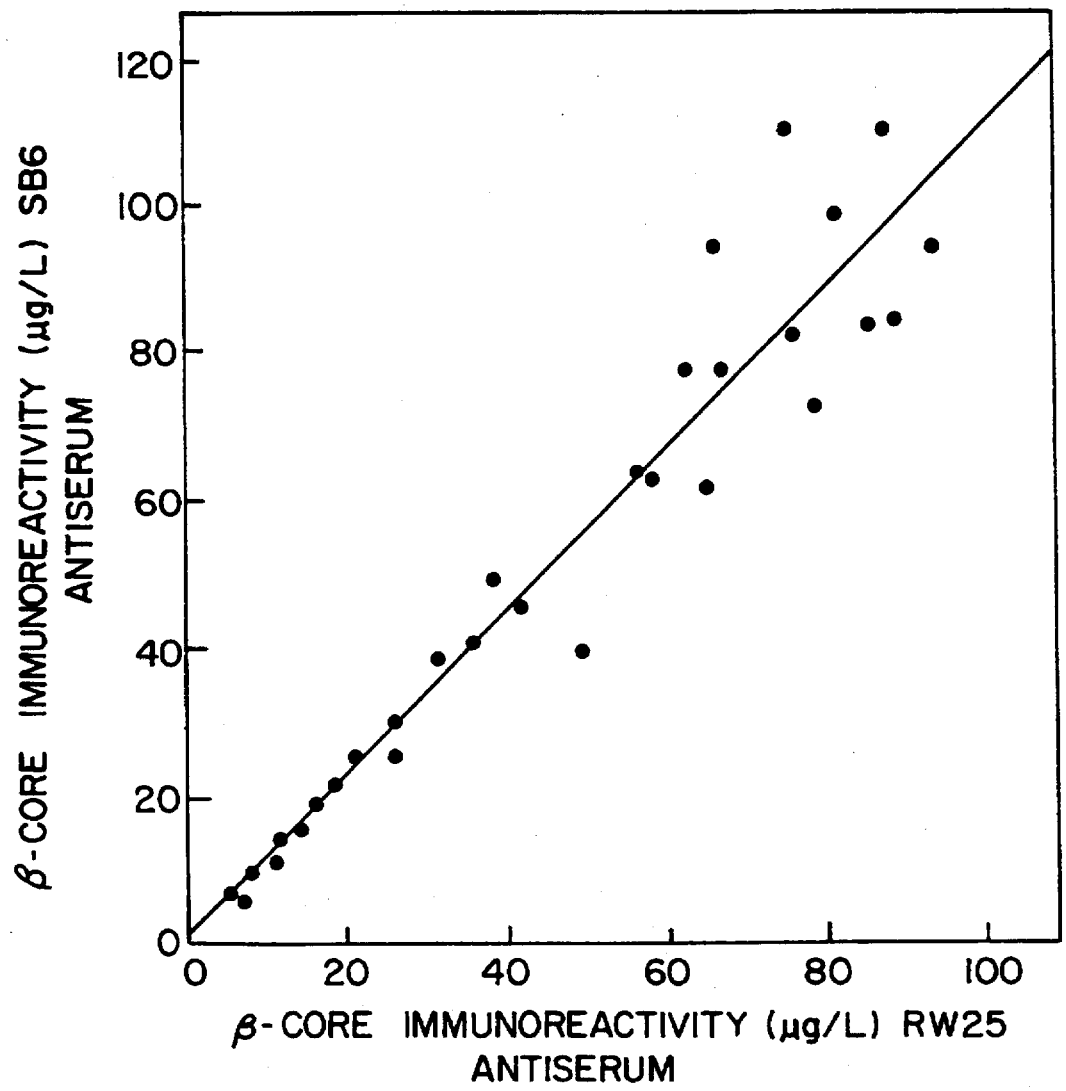
FIG. 9. Correlation of values of β-core immunoreactivity in the individual Sephadex G-100 elution fractions (59–71) of urine from pregnant women determined by RIAs using the SB6 and RW25 antisera.

The cross-reactivities of hCG-related proteins other than the β-core fragments in pregnancy urine were assessed in part by measuring β-core immunoreactivity in fractions from Sephadex G-100 filtration of urine obtained from pregnant women (FIG. 8). Analysis of the fractions in the β-core RIA revealed a single peak of immunoreactive material in the elution position of the purified β-core. In contrast, analysis of the fractions in the hCG (SB6) RIA disclosed extensive immunoreactivity of molecules eluting in the region of hCG and β-subunit (FIG. 8) in addition to immunoreactivity in the region of β-core. It was estimated that in these two urine samples, β-core molecules were responsible for about 80% of the total hCG-like immunoreactivity, as measured by hCG (SB6) RIA. After fractionation on Sephadex G-100, values for immunoreactivity in the β-core peak determined by the β-core RIA (RW25 antiserum) correlated closely with values determined by an SB6 RIA system using β-core as iodinated radioligand and reference preparation (r=0.961; P<0.0001; FIG. 9). The equation of the regression curve calculated by the method of York (York D, 1968, Least squares fitting of a straight line with correlated errors, *Earth Planetary Sci Lett* 5:320) was y=(1.151±0.579)+ (1.056±0.036)×(values are mean ±SD). The slope and y-intercept were not significantly different from 1 and 0, respectively.

Figure 10:
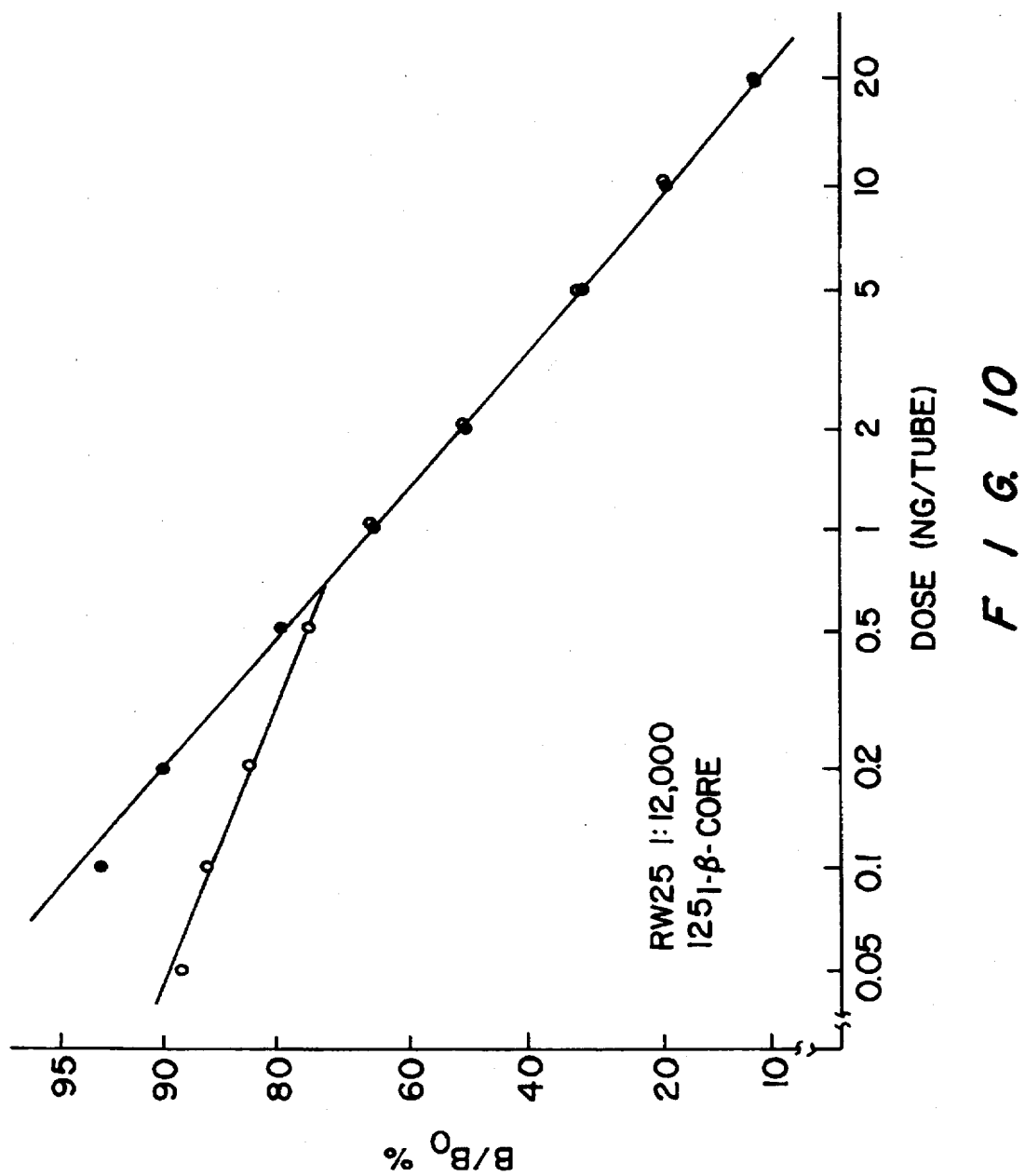
FIG. 10. Dose-response curves of β-core fragment in RIA buffer (●) and a pool of urine from normal boys (200 µL) (O). Binding of radioligand as a percentage of binding at zero dose (B/BO) in buffer is shown on the vertical axis; the dose is given on the horizontal axis.

Matrix effect, blank value, and sensitivity of RIA of urine:

The inhibition curves for purified β-core in RIA buffer and in a pool of urine from normal boys are shown in FIG. 10. A nonspecific urine effect (matrix effect) was found when 200 µL urine were included in the assay system, giving a dog-leg shape at low doses of β-core (0.05–0.06 ng/tube) when dose was plotted on a log scale. The nonspecific counts in assay tubes with and without normal urine were nearly identical.

The present inventors assayed a pool of urine samples from 6 normal boys in 15 replicates in a single assay and found a blank value of 0.20±0.04 (±SD) ng/tube, i.e. 1.0±0.20 µg/L, when a urine volume of 200 µL was assayed. A similar analysis of a pool of urine samples from 22 normal men in eight replicates in the same assay yielded a blank value of 0.60±0.04 ng/tube, i.e. 3.0±0.2 µg/L.

The sensitivity of the RIA was determined by adding increasing amounts of purified β-core to normal human urine. Assays were performed in eight replicates at 0.05, 0.1, 0.2, 0.5, and 1 ng/tube, and the means and SDs were calculated. The SD was constant at 0.04 ng/tube up to 0.5 ng/tube. The present inventors calculated the quantitative detection limit, defined (Currie, L A, 1968, Limits of qualitative detection and quantitative determination, Application to radiochemistry, *Anal Chem* 40:586; Scholler R, 1977, Controls de Qualité en Hormonologie. I. Steroides Urinaires, Paris/Fresnes, Sociéte d'Etudes de Publicités et d'Editons Paris, p 31) as 14.1 times the SD of the blank value, to be 0.56 ng/tube or 2.82 µg/L.

Accuracy:

Accuracy was assessed by adding increasing amounts of purified β-core to aliquots of a pool of urine from normal boys. For each dose (varying from 0.05–20 ng/tube) determinations were performed in eight replicates. The calculated regression curve (n=72 values) was represented by the equation y=a+bx, with a=0.199±0.055 (±SD) and b=1.002±0.008. The value for the slope was not significantly different from 1 (recovery was ~100%), and the y-intercept was not different from the blank value, confirming the existence of a constant error. Because a and b are two dependent parameters, a joint 95% confidence ellipse (Scholler R, 1977, Controls de Qualité en Hormonologie. I. Steroides Urinaires, Paris/Fresnes, Sociéte d'Etudes de Publicités et d'Editons Paris, p 31) was calculated after subtracting the blank value at each level. The slope and y-intercept were not significantly different from 1 and 0, respectively.

Accuracy was further evaluated by a dilution test of a urine sample from a pregnant woman. Aliquots were serially diluted in normal urine up to a final dilution of 1:1024, yielding a range of doses from 0.5–30 ng/tube; the dilutions were assayed in four replicates. The calculated regression curve was represented by the equation y=a+bx, with a=0.132±0.269 and b=1.016±0.021. The slope was not different from 1, and the y-intercept was not different from the blank value. After subtracting the blank value at each level, the slope and y-intercept were not significantly different from 1 and 0, respectively, using a joint 95% confidence ellipse (Scholler R, 1977, Controls de Qualité en Hormonologie. I. Steroides Urinaires, Paris/Fresnes, Sociéte d'Etudes de Publicités et d'Editons Paris, p 31).

Precision:

Precision was evaluated by assaying the same urine samples in a single series (intraassay variability) and in different series (interassay variability). The method was highly reproducible (see Table 4 below).

TABLE 4

Evaluation of the Precision of the β-core RIA

| Intraassay Variability | | | | Interassay Variability | | |
|---|---|---|---|---|---|---|
| n | Mean level (ng/tube) | SD | CV(%) | n | Mean level (ng/tube) | SD | CV(%) |
| 8 | 0.60 | 0.040 | 6.5 | 9 | 0.64 | 0.092 | 14.4 |
| 8 | 1.57 | 0.070 | 4.5 | | | | |
| 8 | 2.77 | 0.146 | 5.3 | 9 | 2.37 | 0.155 | 6.5 |
| 8 | 5.90 | 0.173 | 2.9 | | | | |
| 8 | 10.78 | 0.540 | 5.0 | 9 | 10.81 | 0.983 | 9.1 |

CV, Coefficient of variation.

Figure 11:
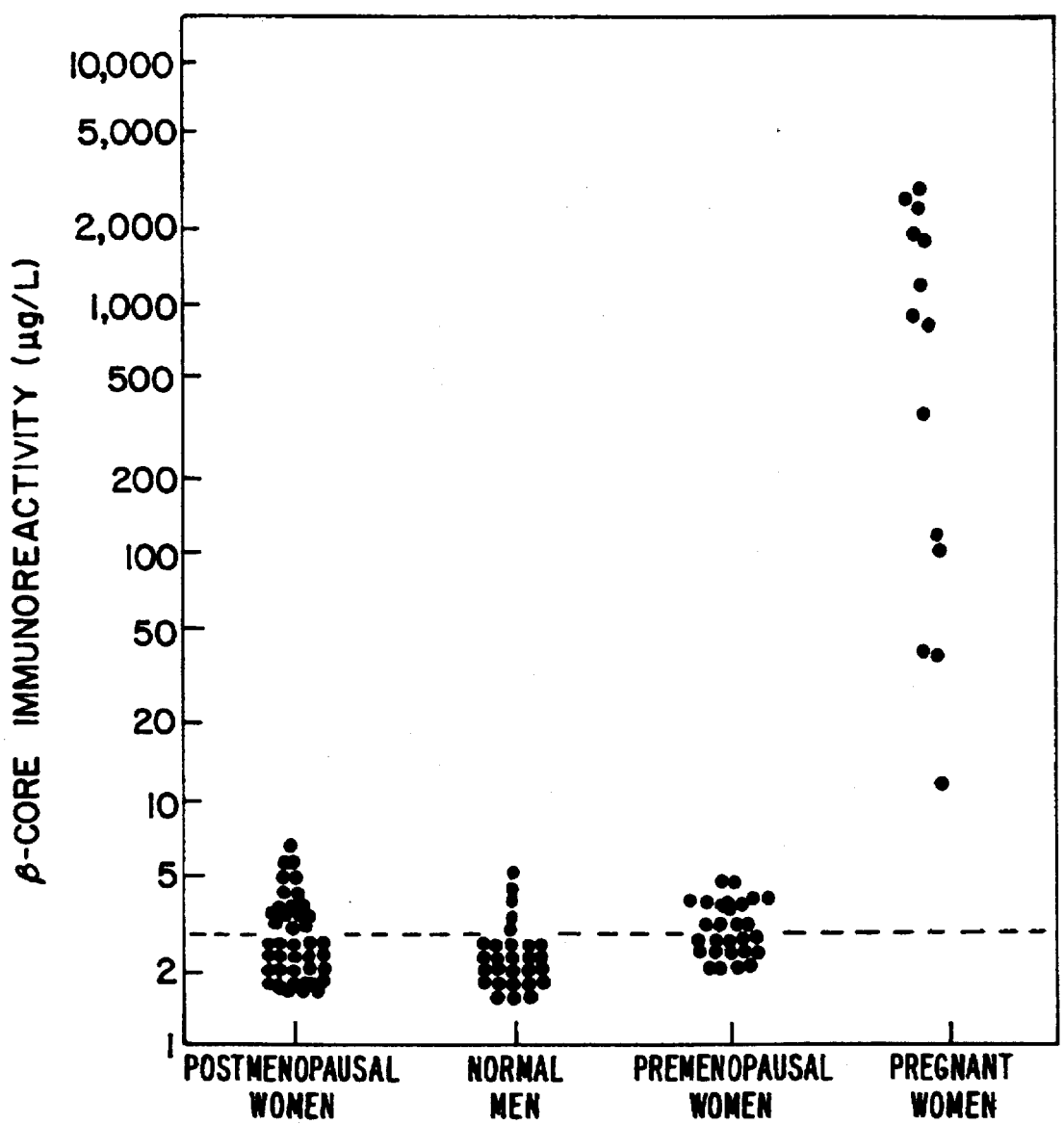
FIG. 11. Concentration of β-core immunoreactivity in urine of post-menopausal women, men, premenopausal women, and pregnant women. The dashed line indicates the quantitative detection limit in urine, determined as described in Currie L A, 1968, Limits of qualitative detection and quantitative determination. Application to radiochemistry, Anal Chem 40:586; and Scholler R, 1977, Controle de Qualité en Hormonologie. I. Steroides Urinaires, Paris/Fresnes, Sociéte d'Etudes de Publicités et d'Editons Paris, p. 31.

Concentrations of β-core immunoreactivity in urine of normal subjects and patients with malignant tumors:

Urinary β-core concentrations in individual postmenopausal women, normal men, and premenopausal women are shown in FIG. 11. Forty-one percent, 18%, and 50% of individual values for postmenopausal women, men, and premenopausal women, respectively, were above the quantitative limit of detection of 2.82 µg/L. For those concentrations that were above this limit, the mean values were 4.12±1.04 (±SD), 3.83±0.85, and 3.57±0.47 µg/L for postmenopausal women, normal men, and premenopausal women, respectively, and were not statistically different from each other.

To determine whether the low level of immunoreactivity in normal urine represents detectable β-core, 0.8 L urine (containing more than 1600 ng β-core immunoreactivity) from two postmenopausal women was processed using an acetone extraction procedure (Reiter E O, et al., 1973, Preparation of urine containing small amounts of FSH and LH for radioimmunoassay: comparison of the kaolin-acetone extraction techniques, J Clin Endocrinol Metab 36:661). After gel filtration of the concentrate on Sephadex G-100, less than 20 ng (~1%) of the original β-core immunoreactivity was recovered in the elution position of purified β-core. In contrast, the recovery of purified β-core by this procedure was 60-80%. Thus, the vast majority of the apparent β-core immunoreactivity in the urine of normal subjects is nonspecific and not identical to β-core.

The concentrations of β-core immunoreactivity in unfractionated urine from pregnant women ranged from 11–4,000 µg/L (FIG. 11). In contrast, urine from nonpregnant women and men contained less than 6.5 µg/L β-core immunoreactivity.

Urinary β-core concentrations in five men with testicular cancer ranged from 37–26,000 µg/L. The β-core concentration in the urine of the patient with a hepatoma was 2,114 µg/L, while the serum hCG level measured by an assay directed to the intact molecule was undetectable (<1 IU/L). Measurable levels (~170 µg/L) of free β-subunit were detectable in this patient's serum.

To compare the molar ratios of β-core and hCG in pregnancy urine, the β-core mol wt was estimated to be about 10,000. This estimate was based on the following: 1) a preliminary report of its peptide structure as consisting of β-subunit residues 6–40 disulfide-bridged to residues 55–92 [Birken S, et al., The structure of the hCG beta core fragment present in human pregnancy urine, 68th Annual Meeting of The Endocrine Society, Anaheim, Calif., 1986, p 159 (Abstract)], giving a peptide mol wt of about 7,300; and 2) the present data indicating the virtual absence of sialic acid and galactose from its oligosaccharide portion, but retention of trimannosyl structures, yielding a carbohydrate mol wt of about 3,000. Thus, the concentrations of β-core in pregnancy urine range from about 1–400 nM. The mol wt of hCG is about 37,000 [Birken S, et al., 1980, Chemistry and immunochemistry of human chorionic gonadotropin, In Segal S J (ed) Chorionic Gonadotropin. Plenum Press, New York, p 65], and since typical peak concentrations of urinary hCG during pregnancy range from 2–10 mg/L (or ~55–270 nM) (Schroeder H K, et al., 1983, Specificity of human β-choriogonadotropin assays for the hormone and for an immunoreactive fragment present in urine during normal pregnancy, Clin Chem 29:667; Marshall J R, et al., 1968, Plasma and urinary chorionic gonadotropin during early human pregnancy, Obstet Gynecol 32:760; Norman R J, et al., 1985, Monoclonal antibodies to human chorionic gonadotropin: implications for antigenic mapping, immunoradiometric assays, and clinical applications, J Clin Endocrinol Metab 61:1031), the present data indicate that β-core is present in pregnancy urine in amounts that are comparable to or in excess of those of hCG.

Discussion:

A RIA for the core fragment of hCGβ was developed that, on a mass basis, has less than $2 \times 10^{-4}$ (wt/wt) cross-reactivity with purified hTSH, hLH, and hFSH, and less than $3 \times 10^{-3}$ (wt/wt) cross-reactivity with purified preparations of intact hCG and its subunits, hCGα and hCGβ. Chromatography of urine from pregnant women demonstrated that levels of hCG up to 90 µg/L in the eluted fractions has no cross-reactivity in the β-core RIA. After fractionation of pregnancy urine by Sephadex G-100 chromatography, there was excellent correlation between the values for β-core concentration determined by RIA with the RW25 antiserum and those with the SB6 antiserum.

Since β-core molecules have different potencies depending on the RIA system used (Schroeder H K, et al, 1983, Specificity of human β-choriogonadotropin assays for the hormone and for an immunoreactive fragment present in urine during normal pregnancy, Clin Chem 29:667; Masure H R, et al, 1981, Characterization of a small molecular size urinary immunoreactive human chorionic gonadotropin (hCG)-like substances produced by normal placenta and by hCG-secreting neoplasms, J Clin Endocrinol Metab 53:1014) it has been difficult to quantify this fragment in urine of pregnant women and patients with hCG-secreting tumors. The above data indicate that β-core can contribute as much as 90% of the total hCG immunoreactivity measured by some assays in urine of pregnant women, in accord with estimates calculated by others (Schroeder H K, et al, 1983, Specificity of human β-choriogonadotropin assays for the hormone and for an immunoreactive fragment present in urine during normal pregnancy, Clin Chem 29:667).

The utility of the hCG (SB6) RIA is somewhat limited by the cross-reactivity of hLH and hLH metabolites in urine, which is most marked in postmenopausal women or in premenopausal women during ovulation (Wehmann R E, et al, 1981, Convenient radioimmunoassay for urinary human choriogonadotropin without interference by urinary human lutropin, Clin Chem 27:1997). In the β-core RIA, the levels of immunoreactivity in urine of postmenopausal women did not differ significantly from those in the urine of normal men. Therefore, hLH and hLH metabolites do not appear to cause the same problem of specificity in the β-core RIA as they do in the hCG (SB6) RIA (Vaitukaitis J L, et al, 1972, A radioimmunoassay which specifically measures human chorionic gonadotropin in the presence of human luteinizing hormone, Am J Obstet Gynecol 113:751; Wehmann R E, et al, 1981, Convenient radioimmunoassay for urinary human choriogonadotropin without interference by urinary human lutropin, Clin Chem 27:1997).

2. Preparation of Polyclonal Antiserum RW37

Materials and Methods:

The polyclonal antiserum RW37 was obtained using identical materials and procedures as described above with reference to the preparation of RW25, with the exception that a different New Zealand White female rabbit (4–6 kg) was used.

Figure 12:
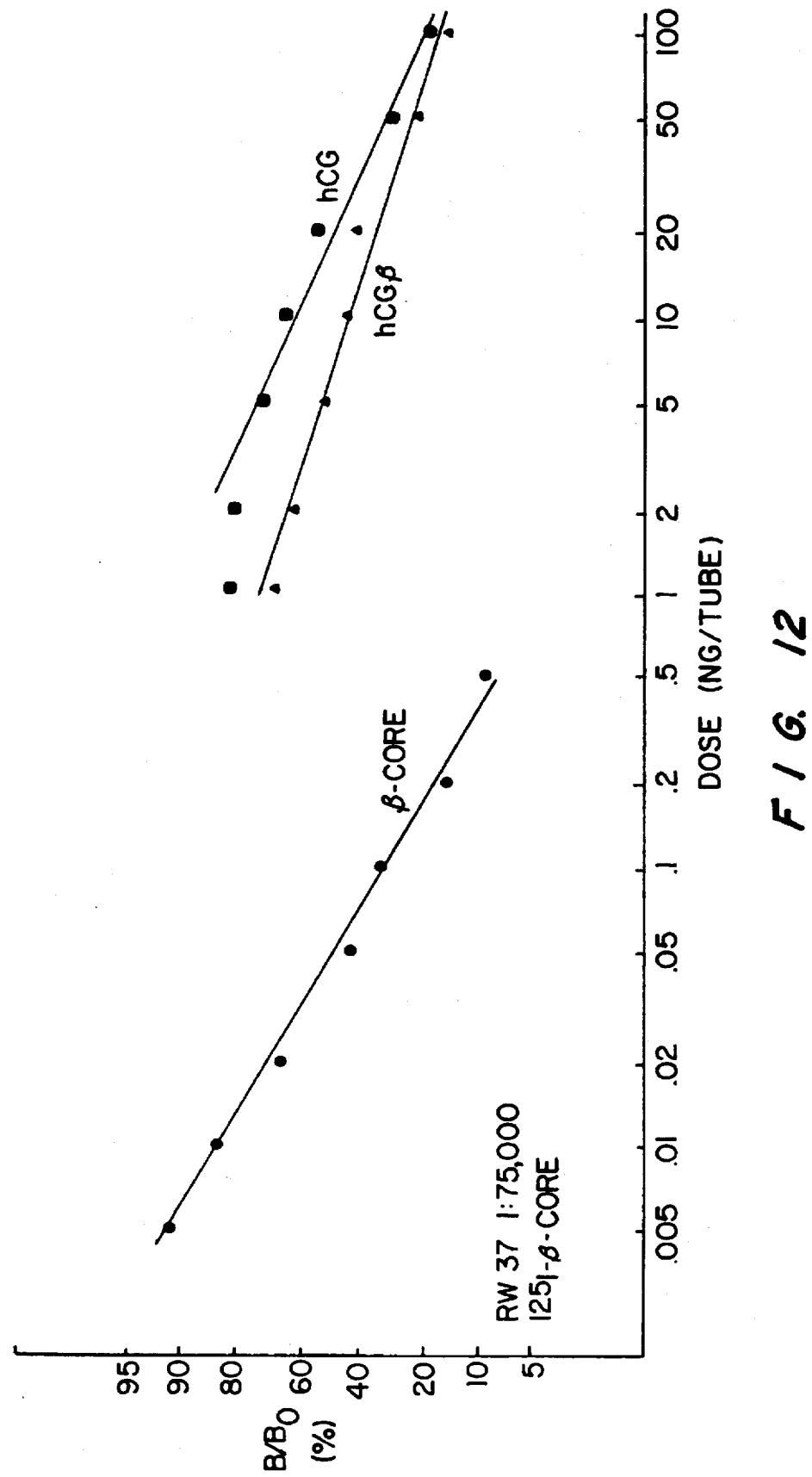
FIG. 12. Dose response curve for hCG, hCGβ and β-core in a RIA using RW37 as the antisera (1:75,000) and [$^{125}$I] β-core as tracer. Binding of radioligand as a percentage of binding at zero dose (B/B$_o$) in buffer is shown on the vertical axis; the dose is given on the horizontal axis.
Figure 13:
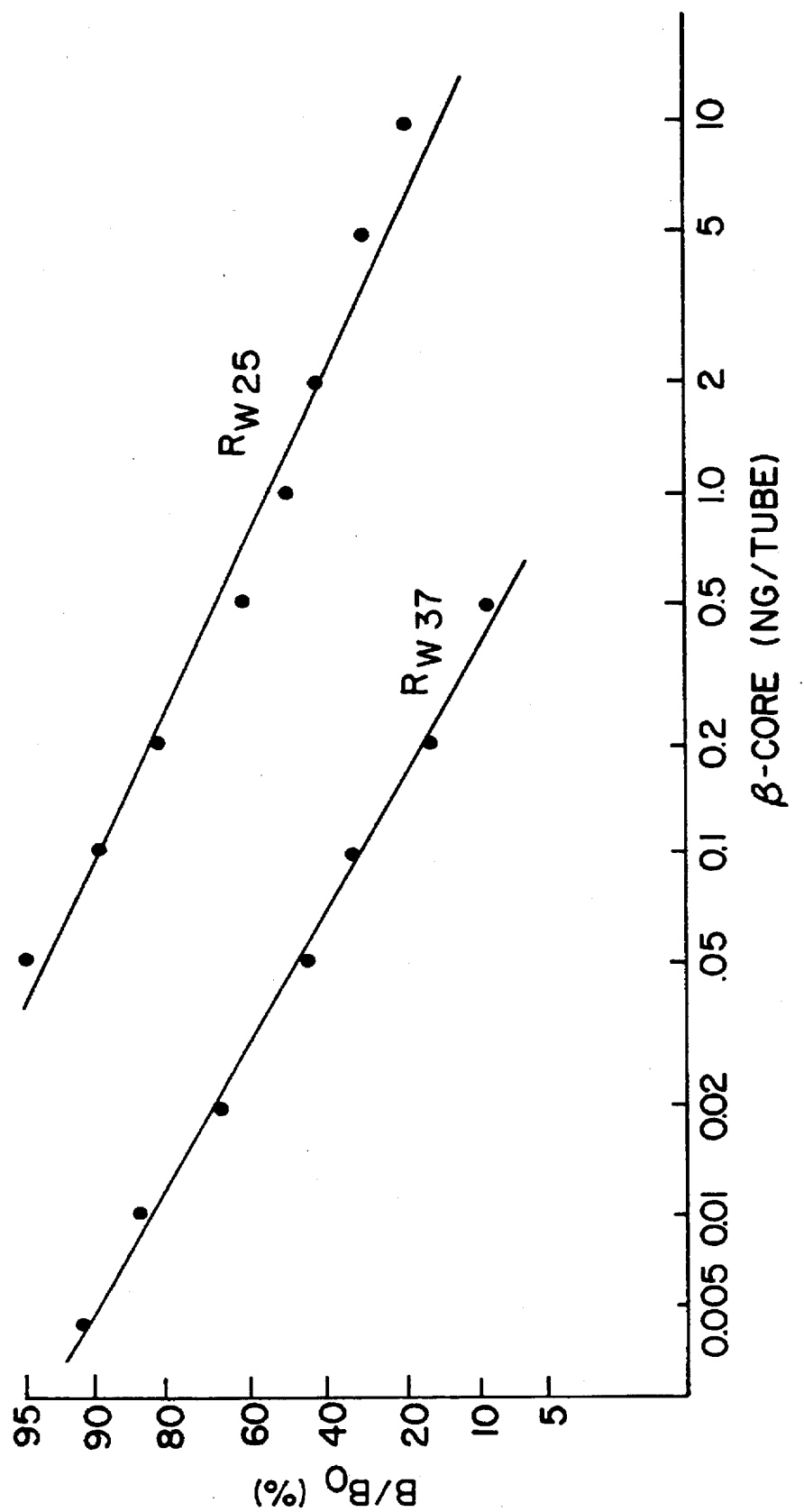
FIG. 13. Comparison of RW37 and RW25 in a dose response curve for β-core. RW37 (1:75,000) and RW25 (1:12,000). Binding of radioligand as a percentage of binding at zero dose (B/B$_o$) in buffer is shown on the vertical axis; the dose is given on the horizontal axis.

Results:

Development of the RW37 antiserum represents a significant advancement over the achievements of RW25, which itself represents a major advance in the field of β-core measurement. RW37 has extremely high specificity for the β-core molecule (less than 0.2% cross-reaction with intact hCG or free β-subunit). See FIG. 12 for the dose response curve of RW37 for hCG, hCGβ and β-core in a RIA using RW37 as the antisera (1:75,000) and [$^{125}$I]B-core as tracer. In addition, RW37 has a five to six-fold higher titer for β-core than RW25, such that RW37 is used at a final dilution of 1:75,000. The sensitivity of RW37 is increased five to ten-fold over that of RW25, resulting in a dose response curve for β-core from 5 pg/tube to 2,000 pg/tube with an ED50 value of 200 pg. RW37 is relatively unaffected by the nonspecific matrix effects commonly observed in biological samples. The range of apparent β-core in normal individuals is 0 to 1 ng/ml of urine, with values for most individuals of less than 0.2 ng/ml. See FIG. 13 for a comparision of RW37 and RW25 in a dose response curve for β-core.

While the invention has been described with respect to certain specific embodiments, it will be appreciated that many modifications and changes may be made by those skilled in the art without departing from the spirit of the invention. For example, it will be clear to one of ordinary skill in the art from a reading of the foregoing that the invention also relates to non-human chorionic gonadotropin. It is intended, therefore, by the appended claims to cover all such modifications and changes as fall within the true spirit and scope of the invention.

We claim:

1. Chorionic gonadotropin β-core molecule in pure form, said molecule having an apparent molecular weight of about 17,500 daltons on SDS-PAGE under non-reducing conditions and having from two to three fragments of apparent molecular weights of about 8,000, 6,000 or 3,500 on SDS-PAGE under reducing conditions, said β-core molecule being substantially free of sialic acid and galactose moieties.

2. A chorionic gonadotropin β-core molecule in pure form in accordance with claim 1, which molecule consists essentially of two polypeptide chains and two carbohydrate moieties of formula:

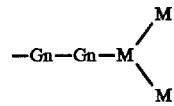

wherein Gn is N-acetylglucosamine, and M is mannose wherein a first of said two polypeptide chains has an amino acid sequence corresponding to amino acids 6–40 of human chorionic gonadotropin β subunit and a second of said two polypeptide chains has an amino acid sequence corresponding to amino acids 55–92 of human chorionic gonadotropin β subunit.

3. A chorionic gonadotropin β-core molecule in accordance with claim 1, said β-core molecule being isolated from humans.

* * * * *